US011099151B2

(12) United States Patent
Holmström et al.

(10) Patent No.: US 11,099,151 B2
(45) Date of Patent: Aug. 24, 2021

(54) OXYGEN SENSOR

(71) Applicant: neoSense Technologies AB, Kista (SE)

(72) Inventors: Nils Holmström, Järfälla (SE);
Kenneth Danehorn, Vaxholm (SE)

(73) Assignee: NEOSENSE TECHNOLOGIES AB, Kista (SE)

( * ) Notice: Subject to any disclaimer, the term of this patent is extended or adjusted under 35 U.S.C. 154(b) by 506 days.

(21) Appl. No.: 15/970,008

(22) Filed: May 3, 2018

(65) Prior Publication Data
US 2018/0321181 A1     Nov. 8, 2018

(30) Foreign Application Priority Data

May 5, 2017   (SE) .................................... 1730127-6

(51) Int. Cl.
| | | |
|---|---|---|
| *G01N 27/404* | (2006.01) | |
| *A61B 5/145* | (2006.01) | |
| *G01N 27/49* | (2006.01) | |
| *A61B 5/00* | (2006.01) | |
| *A61B 5/1468* | (2006.01) | |

(Continued)

(52) U.S. Cl.
CPC ......... *G01N 27/404* (2013.01); *A61B 5/1468* (2013.01); *A61B 5/14542* (2013.01); *A61B 5/7225* (2013.01); *G01N 27/49* (2013.01); *G01N 33/4925* (2013.01); *A61B 2560/0468* (2013.01);

(Continued)

(58) Field of Classification Search
CPC combination set(s) only.
See application file for complete search history.

(56) References Cited

U.S. PATENT DOCUMENTS

| 4,198,851 A | * | 4/1980 | Janata | ................ G01N 27/4143 |
| | | | | 205/782.5 |
| 4,269,684 A | | 5/1981 | Zick | |

(Continued)

OTHER PUBLICATIONS

Nomogram for temperature correction or electrode calibration during PO2 measurements; J. Hedley-Whyte, E. P. Radford JR., and M. B. Laver, Journal of Applied Physiology, vol. 20, No. 4, Jul. 1, 1965 https://doi.org/10.1152/jappl.1965.20.4.785 (Year: 1965).*

(Continued)

*Primary Examiner* — Christian Jang
*Assistant Examiner* — Karen E Toth
(74) *Attorney, Agent, or Firm* — Porter Wright Morris & Arthur LLP

(57) ABSTRACT

An oxygen sensor (1, 2, 3, 4, 5) comprises a working electrode (WE) and a comparatively larger Ag/AgCl reference electrode (RE). A floating voltage between the electrodes (WE, RE) is temporarily retained and a measurement voltage is applied to between the electrodes (WE, RE) during a first period to cause reduction of oxygen and production of an evoked current at the working electrode (WE). The temporarily retained floating voltage is then applied between the electrodes (WE, RE) during a second period to produce a current out from the working electrode (WE). The $pO_2$ in a liquid medium is then representative of a measured net charge to the working electrode (WE) equal to a sum of a charge transferred to the working electrode (WE) during at least a last part of the first period and a charge transferred to the working electrode (WE) during at least a last part of the second period.

25 Claims, 14 Drawing Sheets

(51) Int. Cl.
*G01N 33/49* (2006.01)
*G01N 27/403* (2006.01)

(52) U.S. Cl.
CPC .... *B01L 2300/0645* (2013.01); *G01N 27/403* (2013.01)

(56) References Cited

U.S. PATENT DOCUMENTS

| | | | | |
|---|---|---|---|---|
| 5,376,244 A | * | 12/1994 | Preidel | C12Q 1/001 205/786 |
| 5,562,815 A | | 10/1996 | Preidel | |
| 6,091,292 A | * | 7/2000 | Higashiyama | H03F 3/217 330/10 |
| 6,153,069 A | * | 11/2000 | Pottgen | G01N 27/3273 204/400 |
| 6,236,873 B1 | | 5/2001 | Holmström | |
| 6,321,101 B1 | * | 11/2001 | Holmstrom | A61N 1/36557 204/406 |
| 6,447,670 B1 | * | 9/2002 | Holmstrom | G01N 27/4163 204/402 |
| 2005/0265094 A1 | * | 12/2005 | Harding | G01N 27/28 365/203 |
| 2010/0010328 A1 | | 1/2010 | Nguyen et al. | |
| 2010/0185252 A1 | | 7/2010 | Björling et al. | |
| 2013/0245412 A1 | | 9/2013 | Rong et al. | |
| 2017/0273610 A1 | | 9/2017 | Suri et al. | |

OTHER PUBLICATIONS

Supplementary European Search Report dated Sep. 19, 2018 from corresponding European Application No. 18170476.8.
Burtis et al., Tietz Textbook of Clinical Chemistry and Molecular Diagnostics, 5th Edition, Saunders, pp. 267-272 (2012).
Holmström, Optimal Pacing with an Implantable pO2 Sensor, PhD thesis, KTH Royal Institute of Technology, Stockholm, pp. 1-103 (1999).

* cited by examiner

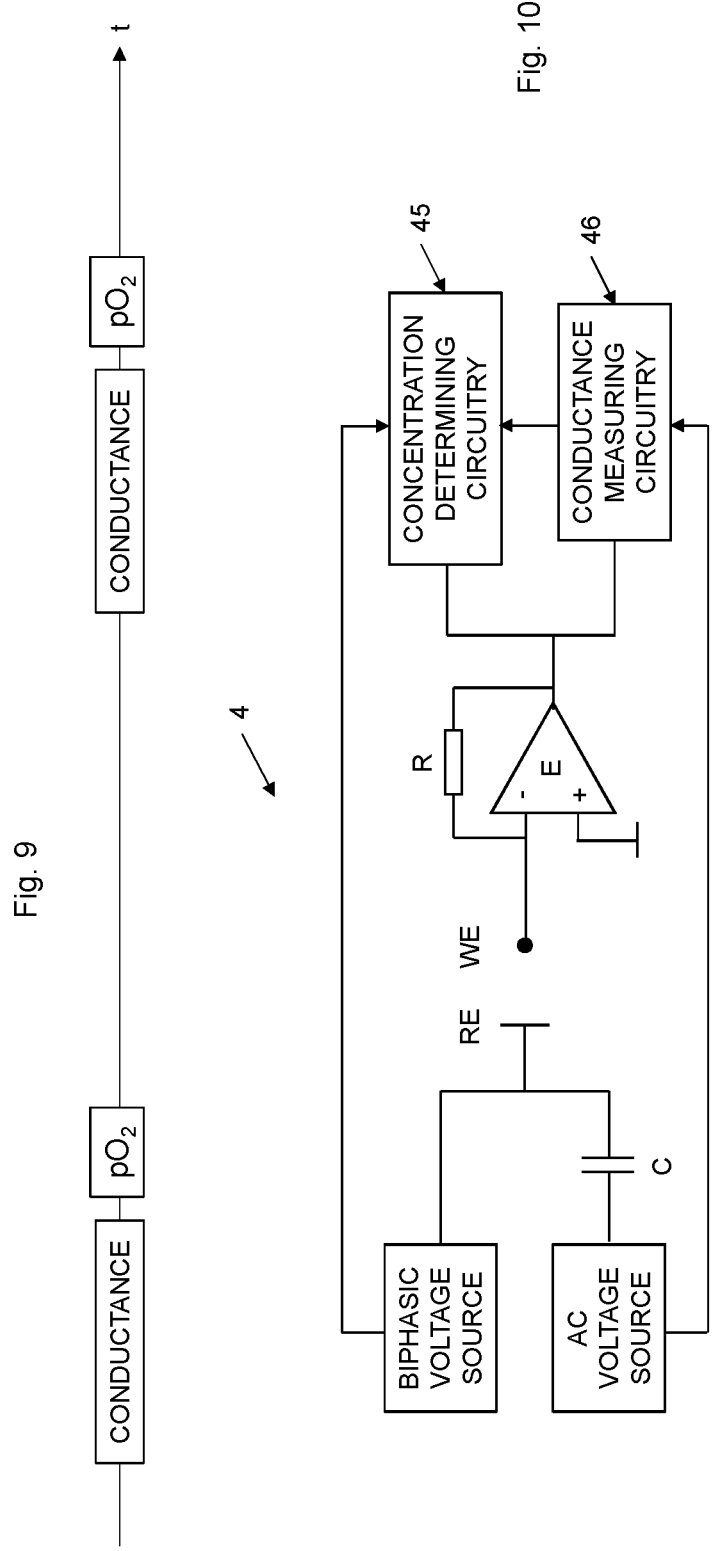

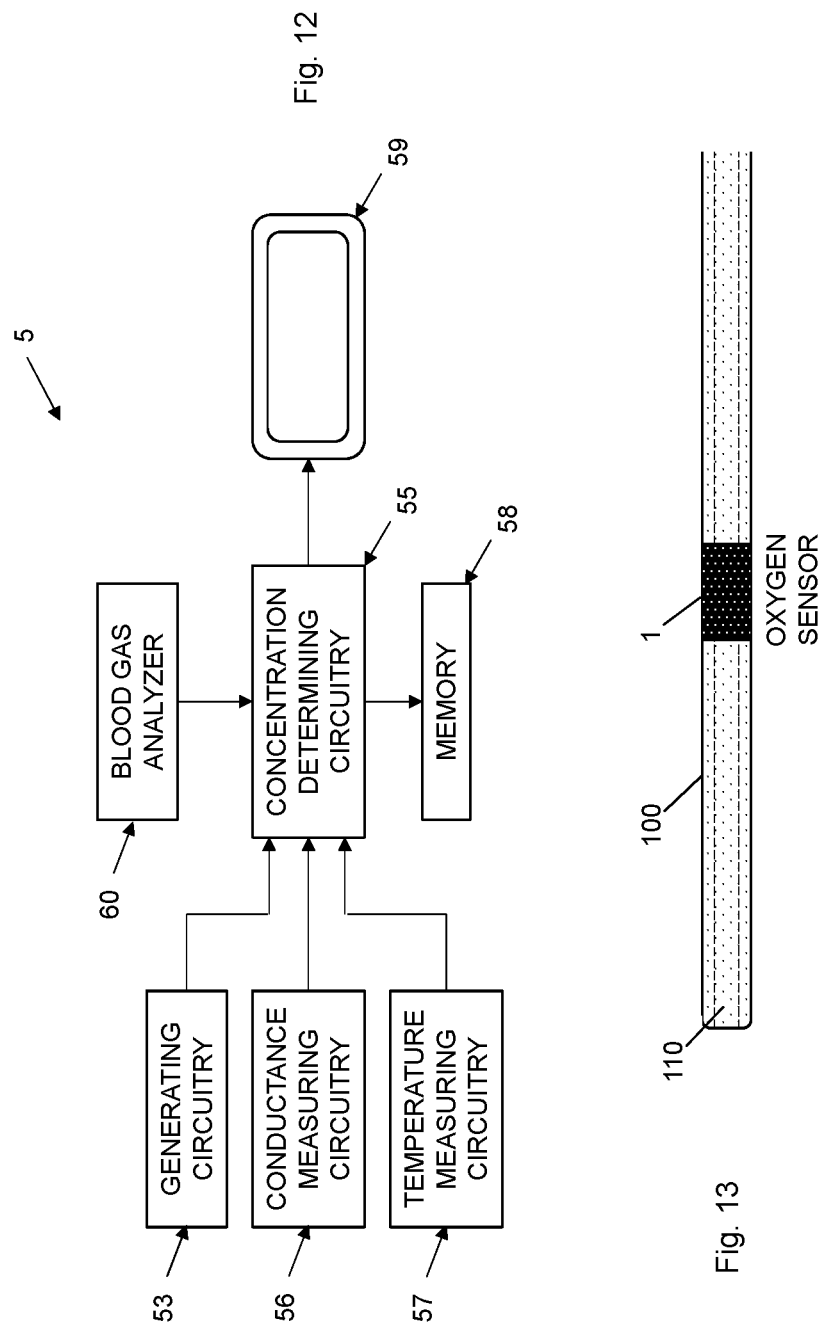

OXYGEN SENSOR

TECHNICAL FIELD

The present embodiments generally relate to an oxygen sensor, and in particular to an oxygen sensor for electrochemical determination of a concentration of dissolved oxygen in a liquid medium.

BACKGROUND

The oxygen tension or partial pressure of oxygen ($pO_2$) is a vital parameter for monitoring blood or cerebrospinal fluid oxygenation in critically ill patients. In the blood environment, dissolved oxygen concentration varies from near anoxic to air saturated. In pressure chambers, the oxygen tension can be further elevated, which has been demonstrated to be a temporary life line for severe anemic patients. Typical oxygen concentrations in blood will have values in the range 0.5-4 ml/l. The solubility of oxygen in 37° C. blood is about 0.03 ml/l*$pO_2$ [mmHg], which gives typical oxygen partial pressures in blood of about 2-18 kPa or 17-133 mmHg.

For intensive care, the requirements and performance of an oxygen sensor is highly dependent on the application. For instance, oxygen sensors deployed on implanted catheters for long-term studies may require a precision better than 1 kPa with calibration against blood gas samples every 4 hours, while short term response to clinical perturbations may require a higher resolution for relative oxygen changes.

An electrochemical oxygen sensor has previously been evaluated for intravascular $pO_2$ measurement in U.S. patent application no. 2010/0010328. The principle was a modified Qlark electrode (Clark, Monitor and control of blood and tissue oxygen tensions, *Transactions—American Society for Artificial Internal Organs*, 1956, 2(1): 41-48) where a small polarizing potential was maintained between a platinum cathode and a silver anode. The electrodes were immersed in an electrolyte solution surrounded by an oxygen-permeable membrane. Oxygen diffused into the chamber, and was reduced at the platinum cathode, producing a current proportional to $pO_2$. The system was, however, complex and unable to deliver a long term stable signal in a clinical environment.

Another principle for oxygen sensor is described in U.S. Pat. No. 6,236,873. The oxygen sensor is designed to eliminate the influence of double-layer capacitance in electrochemical measurements of the concentration of oxygen in blood using a working electrode, a reference electrode and a counter electrode in contact with blood. A big challenge for such a three electrode system has been to create stable and biocompatible electrodes for long time use in blood.

U.S. Pat. No. 6,321,101 discloses a two-electrode device for electrochemical determination of the concentration of at least one dissolved chemical entity in a liquid medium. The device uses a large counter electrode attached to the housing of a pacemaker and a working electrode attached on an electrode lead. The counter electrode potential is in this device also used as reference electrode potential by compensating the measurement voltage for long term variations of the counter electrode potential. A shortcoming with this device is that it can only measure relative changes of $pO_2$ in blood.

U.S. Pat. No. 5,562,815 discloses electrochemical determination of an oxygen concentration with an oxygen sensor that includes a working electrode. The working electrode has a potential profile including three potential steps. The current flowing at the first and second measuring potentials care calculated and integrated over time. One of the two measuring potentials is varied until the two integrals are equal to zero. An oxygen concentration is then determined from the value of the resulting potential.

U.S. Pat. No. 4,269,684 discloses an apparatus for continuously compensating for electrode drift during the measurement of $pO_2$ by the net charge transport technique. The apparatus derives a correction factor from variations in waveforms representing charge returned from an electrochemical cell after successive interrogating voltage pulses.

There is, thus, a need for an efficient oxygen sensor and in particular such an oxygen sensor that can be used to accurately measure oxygen concentrations in a liquid medium for in vivo uses, including monitoring of blood and cerebrospinal fluid oxygen tension.

SUMMARY

It is a general objective to provide an oxygen sensor.

It is a particular objective to provide an oxygen sensor that can be used to accurately measure oxygen concentrations in a liquid medium for in vivo uses, including monitoring of blood and cerebrospinal fluid oxygen tension.

These and other objectives are met by embodiments as disclosed herein.

An aspect of the embodiments relates to an oxygen sensor configured for electrochemical determination of a concentration of dissolved oxygen in a liquid medium. The oxygen sensor comprises a working electrode configured to be in contact with the liquid medium and a reference electrode configured to be in contact with the liquid medium and having i) a surface area that is equal to or larger than a surface area of the working electrode, and ii) a surface made of Ag/AgCl. The oxygen sensor also comprises a retaining circuitry configured to temporarily retain a floating voltage between the working electrode and the reference electrode. The oxygen sensor further comprises a measurement voltage circuitry comprising a voltage source configured to apply a measurement voltage between the working electrode and the reference electrode during a first measurement period causing dissolved oxygen in the liquid medium to react by reduction at a surface of the working electrode to produce an evoked current into the working electrode. The oxygen sensor additionally comprises a floating voltage circuitry configured to apply a voltage between the working electrode and the reference electrode equal to the temporarily retained floating voltage during a second measurement period immediately following and of an equal duration as the first measurement period to produce a current out from the working electrode. The oxygen sensor also comprises a generating circuitry configured to generate a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

Another aspect of the embodiments relates to a method for electrochemical determination of a concentration of dissolved oxygen in a liquid medium. The method comprises temporarily retaining a floating voltage between a working electrode configured to be in contact with the liquid medium and a reference electrode configured to be in contact with the liquid medium and having i) a surface area that is equal to or larger than a surface area of the working electrode, and ii)

a surface made of Ag/AgCl. The method also comprises applying a measurement voltage between the working electrode and the reference electrode during a first measurement period causing dissolved oxygen in the liquid medium to react by reduction at a surface of the working electrode to produce an evoked current into the working electrode. The method further comprises applying a voltage between the working electrode and the reference electrode equal to the temporarily retained floating voltage during a second measurement period immediately following and of an equal duration as the first measurement period to produce a current out from the working electrode. The method additionally comprises generating a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

A further aspect of the embodiments relates to a computer program comprising instructions, which when executed by at least one processor, cause the at least one processor to temporarily retain a floating voltage between a working electrode configured to be in contact with a liquid medium comprising dissolved oxygen and a reference electrode configured to be in contact with the liquid medium and having i) a surface area that is equal to or larger than a surface area of the working electrode, and ii) a surface made of Ag/AgCl. The at least one processor is also caused to control a voltage source to apply a measurement voltage between the working electrode and the reference electrode during a first measurement period causing dissolved oxygen in the liquid medium to react by reduction at a surface of the working electrode to produce an evoked current into the working electrode. The at least one processor is further caused to control the voltage source to apply a voltage between the working electrode and the reference electrode equal to the temporarily retained floating voltage during a second measurement period immediately following and of an equal duration as the first measurement period to produce a current out from the working electrode. The at least one processor is additionally caused to generate a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

A related aspect of the embodiments defines a carrier comprising a computer program according to above. The carrier is one of an electronic signal, an optical signal, an electromagnetic signal, a magnetic signal, an electric signal, a radio signal, a microwave signal, or a computer-readable storage medium.

The oxygen sensor of the embodiments can accurately measure oxygen concentration in a liquid medium, including a body fluid. Hence, the oxygen sensor can be used in vivo, such as for monitoring of blood and cerebrospinal fluid oxygen tension. An advantage of the oxygen sensor is that it is able to provide absolute oxygen concentration values, and is thereby not limited to monitoring relative changes in oxygen concentration. The oxygen sensor furthermore uses stable and biocompatible electrodes, by merely using a working electrode and a reference electrode and is thereby not marred by the prior art problems of designing a stable electrode system consisting of working, counter and reference electrodes.

BRIEF DESCRIPTION OF THE DRAWINGS

The embodiments, together with further objects and advantages thereof, may best be understood by making reference to the following description taken together with the accompanying drawings, in which:

FIG. 9 schematically illustrates synchronous measurement of $pO_2$ and conductance according to an embodiment;

FIG. 10 is a schematic block diagram of an oxygen sensor according to yet another embodiment;

FIG. 12 is a schematic block diagram of an oxygen sensor according to a further embodiment;

FIG. 13 is a schematic block diagram of a catheter comprising an oxygen sensor according to an embodiment;

DETAILED DESCRIPTION

The present embodiments generally relate to an oxygen sensor, and in particular to an oxygen sensor for electrochemical determination of a concentration of dissolved oxygen in a liquid medium.

The oxygen sensor of the embodiments can accurately measure oxygen concentration in a liquid medium, including a body fluid. Hence, the oxygen sensor can be used in vivo, such as for monitoring of blood and cerebrospinal fluid oxygen tension. An advantage of the oxygen sensor is that it is able to provide absolute oxygen concentration values, and is thereby not limited to monitoring relative changes in oxygen concentration as several prior art oxygen sensors. The oxygen sensor furthermore uses stable and biocompatible electrodes, by merely using a working electrode and a reference electrode in clear contrast to several prior art oxygen sensors requiring not only a working electrode and a reference electrode but also a counter electrode.

Figure 1:
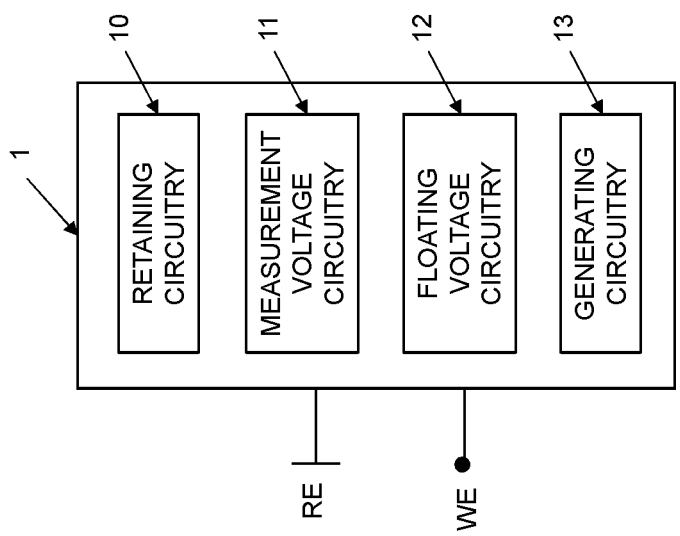
FIG. 1 is a schematic diagram of an oxygen sensor according to an embodiment.

FIG. 1 is a schematic diagram of an oxygen sensor 1 configured for electrochemical determination of a concentration of dissolved oxygen in a liquid medium according to an embodiment. The oxygen sensor 1 comprises a working electrode (WE) configured to be in contact with the liquid medium and a reference electrode (RE) configured to be in contact with the liquid medium. According to the embodiments, the reference electrode has a surface area that is equal to or larger than a surface area of the working electrode. Furthermore, at least the surface of the reference electrode is made of Ag/AgCl.

The oxygen sensor 1 comprises a retaining circuitry 10 configured to temporarily retain a floating voltage between the working electrode and the reference electrode. A measurement voltage circuitry 11 of the oxygen sensor 1 comprises a voltage source configured to apply a measurement voltage between the working electrode and the reference electrode during a first measurement period. The applied measurement voltage causes dissolved oxygen in the liquid medium to react by reduction at a surface of the working electrode to produce an evoked current into the working electrode. The oxygen sensor 1 also comprises a floating voltage circuitry 12 configured to apply a voltage between the working electrode and the reference electrode equal to the temporarily retained floating voltage during a second measurement period immediately following and of an equal duration as the first measurement period. This applied voltage produces a current out from the working electrode. The oxygen sensor 1 further comprises a generating circuitry 13 configured to generate a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

Figure 2:
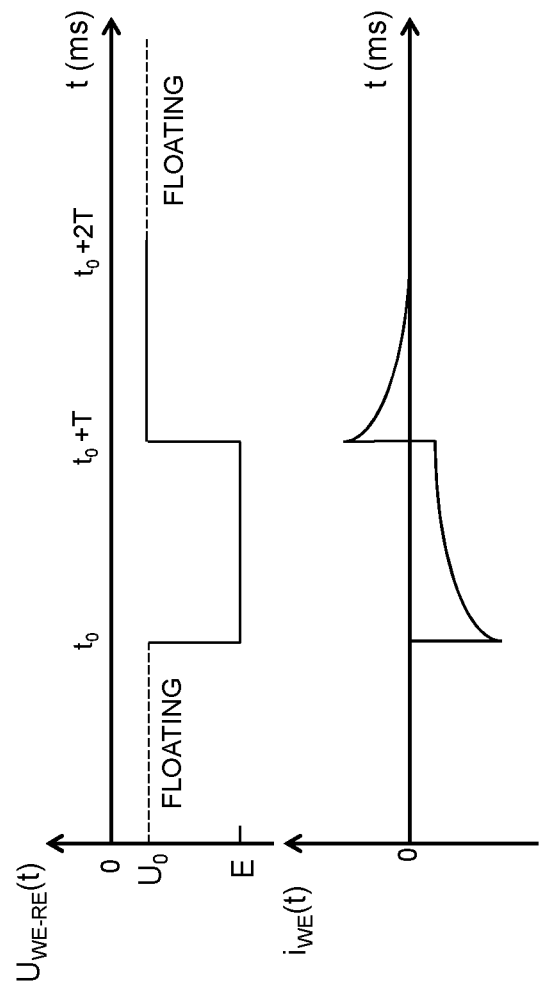
FIG. 2 are voltage and current versus time diagrams for an oxygen sensor according to an embodiment.

The oxygen sensor 1 thereby utilizes a double potential step technique with comparatively long unloaded periods between measurement cycles, i.e., the first measurement period and the second measurement period. This reduces the load on the working and reference electrodes, which in turn increases the longevity of the electrodes and reduces any material transport from the electrodes. FIG. 2 are voltage and current versus time diagrams for an oxygen sensor according to an embodiment. The upper part of FIG. 2 illustrates the working electrode potential in relation to the reference electrode ($U_{WE-RE}(t)$) prior to, during and following the potential steps. The lower part of FIG. 2 illustrates the evoked electrical current ($i_{WE}(t)$).

The measurement cycle consists of two phases or periods of equal duration T. Before each measurement cycle there is a floating voltage between the working electrode and the reference electrode. Such a floating voltage is the potential of the working electrode as related to the reference electrode that the working electrode will acquire when placed in the liquid medium and no current is allowed to pass through the working electrode. This floating voltage or potential is denoted $U_0$ in FIG. 2.

Before the first potential step, i.e., the start of the first measurement period at time $t_0$ in FIG. 2, the floating voltage is temporarily retained or memorized by the retaining circuitry 10. Then, at the start of the first measurement period, the measurement voltage circuitry 11 applies the measurement voltage E between the working electrode and the reference electrode. Thus, after the first potential step of magnitude $E-U_0$, the voltage between the working electrode and the reference electrode is impressed to a sufficient negative voltage E to cause oxygen dissolved in the liquid medium to react by reduction at the surface of the working electrode. Accordingly, oxygen molecules are consumed at the working electrode and a concentration gradient of oxygen will arise. Hydroxide ions are created in the reduction reaction and will migrate towards the reference electrode acting as anode. This migration of hydroxide ions towards the reference electrode in the liquid medium will evoke an electrical current related to oxygen diffusion in the concentration gradient and electrode kinetics at the surface of the working electrode. Both these processes give a current contribution dependent on the oxygen tension in the liquid medium. At the applied measurement voltage E also a double layer capacitance will be recharged, which contributes to the evoked current.

At the end of the first measurement period at time $t_0+T$ in FIG. 2, the potential of the working electrode is turned back to the memorized voltage $U_0$. Accordingly, the amplitude of the second potential step is equal to the amplitude of the first potential step but the two potential steps have opposite directions as shown in the upper part of FIG. 2. Thus, the floating voltage circuitry 12 applies the voltage equal to the temporarily retained floating voltage between the working electrode and the reference electrode during the second measurement period immediately following and of equal duration as the first measurement period.

The evoked current shown in FIG. 2 and floating into the working electrode during the first measurement period contains a contribution that relates to the oxygen concentration and a contribution that relates to charging of the double layer capacitance as mentioned above. The current during the second measurement period floats out from the working electrode and relates only to the double layer charging. Accordingly, when merging the currents to each other only the current related to oxygen concentration remains.

The net charge Q to the working electrode as measured by the generating circuitry 13 is the sum of charge transferred to the working electrode during at least the last parts of the first and second measurement periods. This net charge thereby represents and is indicative of the concentration of dissolved oxygen in the liquid medium.

Between the applied voltage steps, i.e., the first and second measurement periods, the voltage between the working electrode and the reference electrode is floating. At high oxygen tension this voltage returns faster to a voltage closer to zero than at low oxygen tension. This is caused by the amount of oxygen ($O_2$) molecules in the diffusion layer close to the surface of the working electrode. Thus, at high oxygen tension the amplitude of the potential steps is higher than at low oxygen tension, which magnifies the sensitivity of the oxygen sensor. The influence of charging the double layer capacitance will also alter, but this effect is eliminated by having double potential steps with equal magnitude but opposite direction and signs.

In an embodiment, the surface of the working electrode is made of a conductive material selected from a group consisting of gold, silver and carbon. In the latter carbon case, the surface of the working electrode could be made of conductive pyrolityic glassy carbon or graphene as illustrative, but non-limiting, examples. A preferred conductive material is gold.

Thus, in an embodiment at least the surface of the working electrode is made of an inert conductive material. Inert means that the surface material of the working electrode should not be oxidizing or changing its properties at the electrochemical use intended in the oxygen sensor. Thus, the inert conductive material should be stable as long as the potential is kept within potentials described herein, i.e. the floating voltage $U_0$ and the measurement voltage E.

Correspondingly, at least the surface of the reference electrode is made of Ag/AgCl, i.e., Ag and/or AgCl. This conductive material is capable of resisting the anodic load that the reference electrode is exposed to during operation and maintains a stable potential at the intended use.

The average load of the reference electrode will typically not be zero. In clear contrast, there will be a small anodic net current. Accordingly, a small amount of silver will be consumed on the surface by producing silver chloride; $Ag(s)+Cl^-\rightarrow AgCl+e^-$. This Ag/AgCl layer stabilizes the potential of the reference electrode to about 0.2 V vs. a standard hydrogen electrode (SHE). Some AgCl will dissolve slowly into the liquid medium but new AgCl will continuously be produced by the net current load. Hence, the surface of the reference electrode reacts electrochemically with the liquid medium containing chloride ions ($Cl^-$) by release of silver ions ($Ag^+$) from the electrode surface, thereby continuously forming AgCl during use.

Only the surfaces or surface layers of the working and reference electrodes are active in the electrochemical process. Accordingly, the electrodes do not need to be solid gold, silver or carbon material or solid Ag/AgCl material. This means that the active surface layer of gold, silver or carbon, or of Ag/AgCl could be deposited onto another suitable conductive material.

Hence, in an embodiment the working electrode is made of the conductive material selected from the group consisting of gold, silver and carbon, preferably gold. In this embodiment the working electrode is made as a unitary structure of the selected conductive material. In another embodiment, the working electrode is made of conductive base or bulk material and has a surface layer, such as film or coating, deposited onto the conductive base or bulk material. In this embodiment, the surface layer is made of a conductive material selected from the group consisting of gold, silver and carbon. The conductive base or bulk material could then be made of a non-catalytic material, such as platinum or stainless steel.

Correspondingly, in an embodiment the reference electrode is made of Ag/AgCl. In this embodiment the reference electrode is made as a unitary structure of Ag/AgCl. In another embodiment, the reference electrode is made of conductive base or bulk material and has a surface layer, such as film or coating, deposited onto the conductive base or bulk material. In this embodiment, the surface layer is made of Ag/AgCl. The conductive base or bulk material could then be made of a non-catalytic material, such as platinum, gold, or stainless steel.

As mentioned in the foregoing, the surface area of the reference electrode is equal to or larger than the surface area of the working electrode. In an embodiment, the surface area of the reference electrode is larger than the surface area of the working electrode. In a particular embodiment, a relationship or ratio of the surface area of the working electrode and the surface area of the reference electrode is within an interval of from 1:1 to 1:100, preferably within an interval of from 1:1.5 to 1:10, more preferably within an interval of from 1:2 to 1:5, such as equal to 1:2.5.

By having a surface area of the reference electrode that is larger than the surface area of the working electrode the potential change from the floating potential $U_0$ is minimized during excitation, i.e., during the first measurement period. Thus, if the surface area of the reference electrodes is comparatively small, the voltage drop over the electrochemical interface at the reference electrode will be large. This in turn implies that the voltage drop at the working electrode will be reduced with the same voltage. In order to have a working electrode that is sensitive for oxygen, the reduction potential at the working electrode is preferably in the interval of 0.6 to 1.4 V. Having a larger surface area of the reference electrode as compared to the surface area of the working electrode means that the voltage drop at the reference electrode can be assumed to be at least close to zero. If the surfaces areas of the working and reference electrodes instead are, for instance, the same the measurement voltage has to be increased beyond the preferred interval. However, in such a case, the voltage drop at the reference electrode will not be stable and the cross-sensitivity for, among others, temperature and salts in the liquid medium as well as oxidation reactions will be more dominant in the measured net charge.

Thus, having a larger surface area of the reference electrode as compared to the surface area of the working electrode implies that a smaller potential step can be used in the first measurement period, which in turn reduces the influence of other factors, such as temperature and salt concentration in the liquid medium, to the measured net charge. Hence, the accuracy in the determination of the concentration of dissolved oxygen is increased by having a larger surface area of the reference electrode.

The larger surface area of the reference electrode as compared to the surface area of the working electrode could be achieved by having larger dimensions of the reference electrode as compared to the working electrode, such as diameter, length, height, etc. depending on the shapes of the reference and working electrodes.

An alternative, or additional, way of increasing the surface area of the reference electrode is to have a surface that has a surface roughness ($R_a$) that is larger than a surface roughness of the surface of the working electrode.

The increase in surface roughness can, for instance, be accomplished by blasting, such as sand blasting, the Ag surface of the reference electrode, i.e., before application of AgCl to form the Ag/AgCl surface. On the other hand, the surface of the working electrode is preferably polished to very smooth, i.e., have a low surface roughness.

Increased surface area of the reference electrode could also, or alternatively, be accomplished by having a porous surface layer.

In an embodiment, the first and second measurement periods are of equal duration and this duration is selected within an interval of from 5 to 20 ms, preferably within an interval of from 7 to 15 ms, and more preferably equal to 10 ms.

This means that the durations of the first and second measurement periods are quite short with comparatively longer unloaded periods between the measurement occasions. This reduces the load of the electrodes, reduces the material transport at the electrode surfaces and thereby increases the longevity of the electrodes and thereby of the oxygen sensor.

The sampling period, i.e., the duration between measurement occasions, is dependent on the application of the oxygen sensor. However, in most applications the sampling period is at least 50 times, typically at least 100 times, such as several 100 times or even 1000 times, longer as compared to the duration of the first and second measurement periods, i.e., at least 50×T. For instance, the sampling period could be within an interval of from 0.5 to 60 s, such as within an interval of from 0.5 to 30 s, for instance within an interval of from 0.5 to 10 s, such as 1 s.

In an embodiment, the measurement voltage circuitry 11 comprises a constant voltage source configured to output a constant voltage, i.e., the measurement voltage E between the working electrode and the reference electrode, during the first measurement period.

In an embodiment, the measurement voltage circuitry 11 is configured to apply a measurement voltage within an interval of from −0.5 to −1.4 V between the working electrode and the reference electrode during the first measurement period. Other preferred intervals for the measurement voltage include from −0.5 to −1.2 V or from −0.6 to −1.4 V. An example of a suitable measurement voltage is −0.8 V, another suitable measurement voltage is −0.6 V, but also other voltages within the above mentioned interval could be used such as −0.5 V, −0.6 V, −0.7 V, −0.9 V, −1.0 V, −1.1 V, −1.2 V, −1.3 V or −1.4 V.

The reduction of oxygen, i.e., $O_2 + 2H_2O + 4e^- \rightarrow 4\ OH^-$, takes place at +0.4 V. The potential for the Ag/AgCl reference electrode is +0.2 V vs. SHE. In theory, this means that the reduction of $O_2$ would be possible already from +0.2 V vs. Ag/AgCl. However, in practice the charge transport starts from zero at about −0.5 V and increases linearly with more negative potentials. The highest $O_2$ sensitivity is typically at or around −0.8 V vs. Ag/AgCl. This has several causes, among others, that the diffusion rate of $O_2$ increases at higher $O_2$ concentration gradients, the charge transfer increases at higher electrode potentials according Butler-Volmer equation and the migration of ions increases at higher voltages.

In an embodiment, the generating circuitry 13 is configured to generate the signal representative of the concentration of dissolved oxygen in the liquid medium based on a measured net charge to the working electrode equal to a sum of a charge transferred to the working electrode during the first measurement period and a charge transferred to the working electrode during the second measurement period.

Thus, in this embodiment and as shown in FIG. 2, the measured net charge is equal to the sum of the charge transferred to the working electrode during the whole first measurement period and the whole second measurement period.

Figure 3:
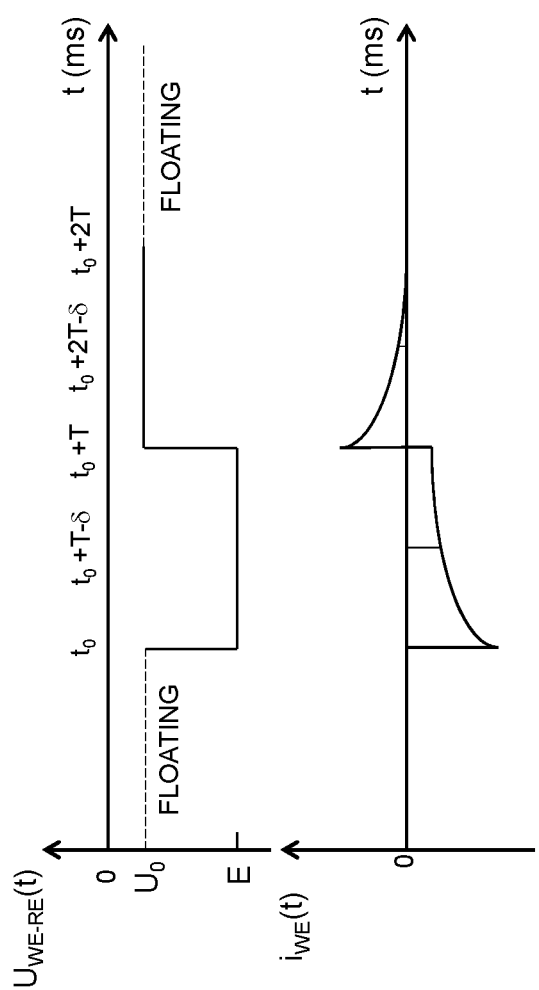
FIG. 3 are voltage and current versus time diagrams for an oxygen sensor according to another embodiment.

In another embodiment and as shown in FIG. 3, the generating circuitry 13 is configured to generate the signal representative of the concentration of dissolved oxygen in the liquid medium based on a measured net charge to the working electrode equal to a sum of a charge transferred to the working electrode during the last part of the first measurement period and a charge transferred to the working electrode during the last part of the second measurement period.

This last period of the first measurement period (from $t=t_0$ to $t=t_0+T$) corresponds to the period from $t=t_0+T-\delta$ to $t=t_0+T$. Correspondingly, the last period of the second measurement period (from $t=t_0+T$ to $t=t_0+2T$) corresponds to the period from $t=t_0+2T-\delta$ to $t=t_0+2T$.

A reason for merely measuring or calculating the charge transferred to the working electrode during the last parts of the first and second measurement periods is to avoid the initial current peaks that may occur due to limitations in the electronics of the oxygen sensor.

In an embodiment, the duration $\delta$ of the last parts of the first and second measurement periods is preferably within an interval of from 0.1T to 0.75T, preferably equal to 0.5T, wherein T denotes the duration of the first and second measurement periods.

The net charge to the working electrode is, in an embodiment, the sum of the integrated charges at the first and second measurement periods, or the last parts thereof. During the first measurement period, the integrated charge includes both the current related to the reduction of oxygen at the working electrode and the current relating to charging the double layer capacitance. During the second measurement period, the integrated charge that has the opposite sign only relates to the double layer charging. The net charge, i.e., the sum of charges, is, thus, proportional to the concentration of dissolved oxygen in the liquid medium.

Figure 4:
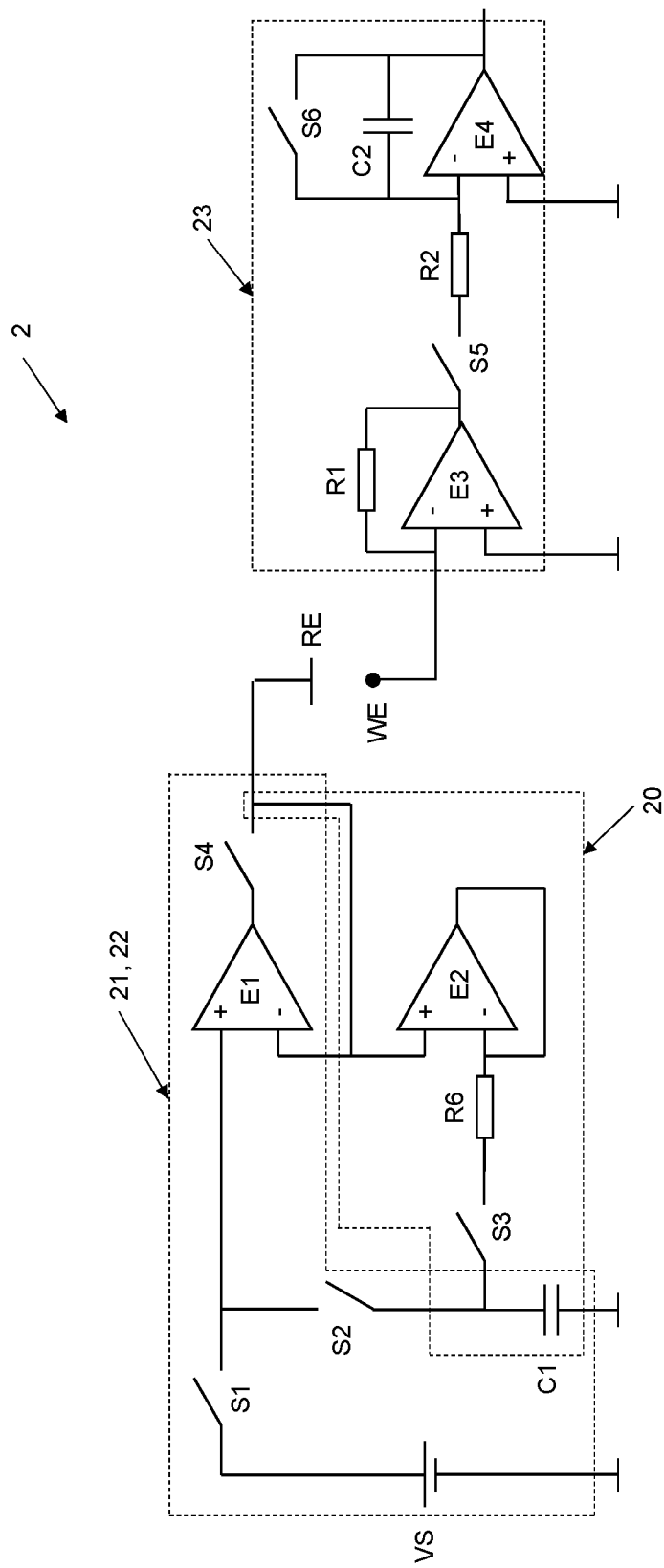
FIG. 4 is a schematic diagram of an oxygen sensor according to another embodiment.

FIG. 4 is a schematic diagram of an oxygen sensor according to an implementation example. In this embodiment, the retaining circuitry 20 of the oxygen sensor 2 comprises a voltage follower E2, in the form of an operational amplifier, having a non-inverting input connected to the reference electrode RE and an output connected to an inverting input of the voltage follower E2. The retaining circuitry 20 also comprises a switch S3 and a capacitor C1 connected between common ground and the switch S3. The switch S3 is connected between the capacitor C1 and the inverting input of the voltage follower E2.

In an embodiment, the retaining circuitry 20 also comprises a resistor R6 connected between the switch S3 and the output of the voltage follower E2. The resistor R6 may, alternatively, be connected between the switch S3 and the capacitor C1.

The resistor R6 and the capacitor C1 form a low pass filter, such as a low pass anti-aliasing filter. This optional low pass filter is arranged to reduce noise and has a cut off frequency well below 50 Hz. For instance, if the resistor R6 has a resistance of 330 kΩ and the capacitor C1 has a capacitance of 100 nF, the cut off frequency of the low pass filter will be 5 Hz.

In the illustrated embodiment of the oxygen sensor 2, the measurement voltage circuitry 21 and the floating voltage circuitry 22 together comprise a first switch S1 and a voltage source VS connected between common ground and the first switch S1. In a particular embodiment, the voltage source VS is a constant voltage source. The measurement voltage circuitry 21 and the floating voltage circuitry 22 also comprise an operational amplifier E1 having a non-inverting input connected to the first switch S1, an inverting input connected to the reference electrode RE and an output connected to the reference electrode via a second switch S4. A third switch S2 is connected between i) a point between the first switch S1 and the non-inverting input of the operational amplifier E1 and ii) the retaining circuitry 20.

The generating circuitry 23 of the illustrated oxygen sensor 2 comprises a current amplifier E3 having a non-inverting input connected to common ground, an inverting input connected to the working electrode WE and an output connected to a first switch S5. A first resistor R1, a so-called feedback resistor R1, is connected between the inverting input of the current amplifier E3 and the output of the current amplifier E3. The generating circuitry 23 also comprises a sample-and-hold circuit and a second resistor R2 connected between the first switch S5 and the sample-and-hold circuit. This sample-and-hold circuit comprises an operational amplifier E4 having a non-inverting input connected to common ground, an inverting input connected to the second resistor R2 and an output. The sample-and-hold circuit also comprises a capacitor C2 connected between the inverting input of the operational amplifier E4 and the output of the operational amplifier E4 and a second switch S6 connected between the inverting input of the operational amplifier E4 and the output of the operational amplifier E4.

Figure 5:
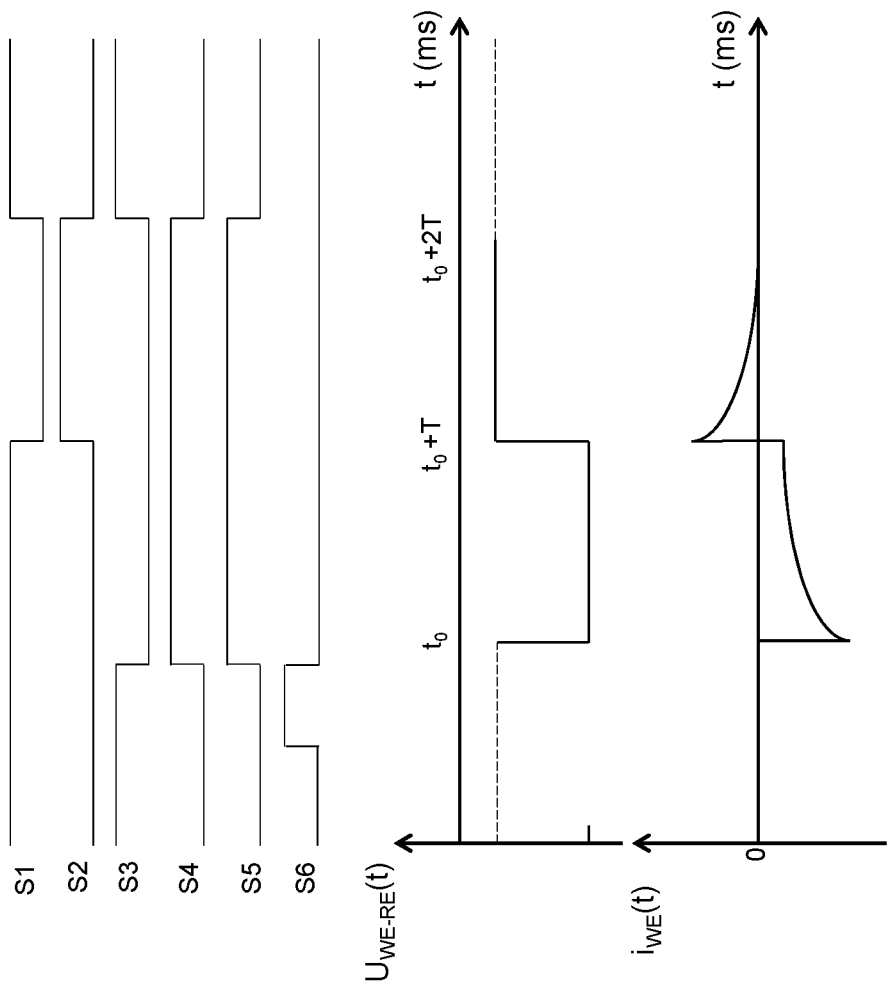
FIG. 5 schematically illustrates states of switches in the oxygen sensor illustrated in FIG. 4 prior to, during and after a measurement cycle according to an embodiment.

FIG. 5 schematically illustrates states of the switches S1 to S6 in the oxygen sensor 2 illustrated in FIG. 4 prior to, during and after a measurement cycle according to an embodiment. In the following 0 indicates that a switch is open and 1 indicates that a switch is closed. In the unloaded state, S1=1, S2=0, S3=1, S4=0, S5=0 and S6=0. In this state unloaded state the floating potential on the reference electrode RE is applied to the non-inverting input of the voltage follower E2. The output of the voltage follower E2 is connected to the capacitor C1 via the closed switch S3. Accordingly, the capacitor C1 is charged to the floating voltage between the reference electrode RE and the working electrode WE. The value of this floating voltage is temporarily retained in the capacitor C1 when the switch S3 is opened. The constant voltage over the capacitor C2 in the sample-and-hold circuit is also present on the output of the operational amplifier E4 in the sample-and-hold circuit. This voltage value corresponds to the previous measurement conducted in a previous measurement cycle.

In the unloaded state, no current is passing through an outer circuit consisting of the working electrode WE, the reference electrode RE and the intermediate liquid medium.

Prior to start of the measurement cycle, the capacitor C2 of the sample-and-hold circuit is temporarily short-circuited by closing the second switch S6. This resets the capacitor C2. Hence, at this point in time the states of the switches are S1=1, S2=0, S3=1, S4=0, S5=0 and S6=1.

At the start of the first measurement period and, in this embodiment, during the whole first measurement period, the switch states are S1=1, S2=0, S3=0, S4=1, S5=1, S6=0. Opening of the switch S3 disconnects the voltage follower E2 from the capacitor C1 and the floating voltage is temporarily retained by the capacitor C1.

Closing switch S4 connects the operational amplifier E1 to the reference electrode RE. Accordingly, the operational amplifier E1 is able to control its output so that the potential on the non-inverting input and the inverting input of the operational amplifier E1 will be the same through negative feedback. At this point, the reference electrode RE has the same voltage as the voltage source VS and the voltage between the working electrode and the reference electrode will be the measurement voltage.

The current i(t) flowing through the resistor R2 will charge the capacitor C2 according to equation (1) to the charge $Q_1$:

$$Q_1 = \int_{t_0}^{t_0+T} i(t)dt \qquad (1)$$

The current is flowing through the resistor R2 only when the switch S5 is closed. If oxygen is reduced at the working electrode, then the current i(t) could be written as a sum of two currents $i(t)=i_p(t)+i_d(t)$, wherein $i_p(t)$ is the current contribution due to the reduction of oxygen at the working electrode and $i_d(t)$ is the current contribution arising from the formation of the double layer capacitance at the measurement voltage.

At the end of the first measurement period and during, in this embodiment, the whole second measurement period the switch states are S1=0, S2=1, S3=0, S4=1, S5=1 and S6=0. At this point, the non-inverting input of the operational amplifier E1 is disconnected from the voltage source VS and is instead connected to the capacitor C1, which is charged by the temporarily retained floating voltage. This means that the reference electrode RE is controlled by the operational amplifier E1 to apply a voltage equal to the floating voltage between the reference electrode RE and the working electrode WE during the second measurement period. The potential step $(E-U_0)$ at this time point $t=t_0+T$ will, thus, be equal in amplitude but opposite in sign as compared to the potential step $-(E-U_0)$ at the time point $t=t_0$.

The current, which is discharging the electrochemical double layer, charges the capacitor C2 with a charge $Q_2$, which is added to the charge $Q_1$, already established on the capacitor C2:

$$Q_2 = \int_{t_0+T}^{t_0+2T} -i_d(t)dt \qquad (2)$$

Accordingly, the net charge $Q=Q_1+Q_2$ is according to equation (3):

$$Q=Q_1+Q_2=\int_{t_0}^{t_0+T}(i_d(t)+i_p(t))dt+\int_{t_0}^{t_0+T}-i_p(t)dt=\int_{t_0}^{t_0+T}i(t)dt \qquad (3)$$

At the end of the second measurement period the switches are once more set to S1=1, S2=0, S3=1, S4=0, S5=0 and S6=0.

The summation of the charges during the first and second measurement periods thereby results in that the charge contributions due to the double layer will cancel. Hence, only the contribution from the reduction of oxygen at the working electrode will remain. The end voltage over the capacitor C2 will be proportional to Q/C2. This value can, thus, be used as representative of the concentration of dissolved oxygen in the liquid medium.

Figure 6:
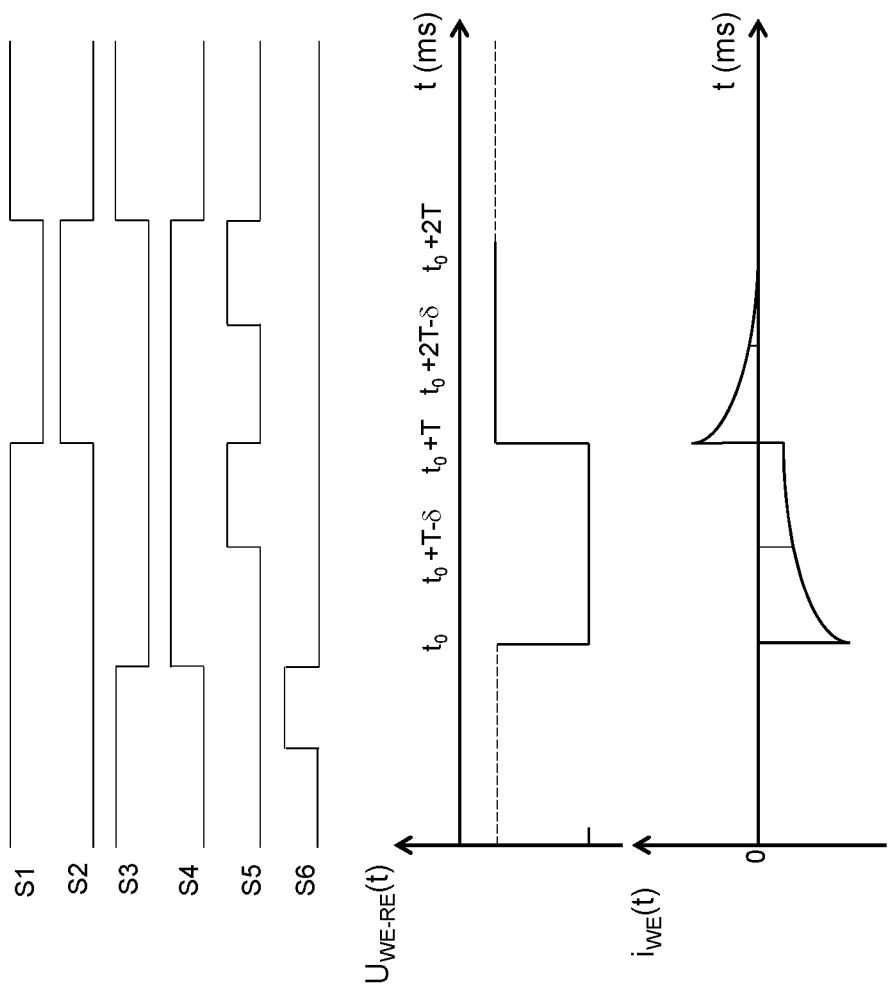
FIG. 6 schematically illustrates states of switches in the oxygen sensor illustrated in FIG. 4 prior to, during and after a measurement cycle according to another embodiment.

In the embodiment discussed above in connection with FIG. 5, the net charge is the sum of charges transferred to the working electrode during the complete first and second measurement periods. FIG. 6 schematically illustrates states of the switches S1 to S6 in the oxygen sensor 2 illustrated in FIG. 4 prior to, during and after a measurement cycle according to another embodiment. In this embodiment, the net charge is instead the sum of charges transferred to the working electrode during the last parts of the first and second measurement periods.

Thus, at the initial part from $t=t_0$ to $t=t_0+T-\delta$ of the first measurement period, the switch states are S1=1, S2=0, S3=0, S4=1, S5=0 and S6=0. This is the same as in FIG. 5 but with the important difference of keeping the switch S5 open during this initial part. Hence, no current is flowing through the resistor R2 and no charging of the capacitor C2 are taking place during this initial part of the first measurement period. During the last part from $t=t_0+T-\delta$ to $t=t_0+T$ of the first measurement period, the switch states are S1=1, S2=0, S3=0, S4=1, S5=0 and S6=0. This means that the capacitor C2 will be charged during this last period.

Correspondingly, at the initial part from $t=t_0+T$ to $t=t_0+2T-\delta$ of the second measurement period the switch states are S1=0, S2=1, S3=0, S4=1, S5=0 and S6=0. This is the same as in FIG. 5 but with the important difference of keeping the switch S5 open during this initial part. Hence, no current is flowing through the resistor R2 and no charging of the capacitor C2 are taking place during this initial part of the second measurement period. During the last part from $t=t_0+2T-\delta$ to $t=t_0+2T$ of the second measurement period the switch states are S1=0, S2=1, S3=0, S4=1, S5=0 and S6=0. This means that the capacitor C2 will be charged during this last period.

The resulting net charge will in this embodiment be equal to:

$$Q=Q_1+Q_2=\int_{t_0+T-\delta}^{t_0+T}(i_d(t)+i_p(t))dt+\int_{t_02T-\delta}^{t_0+2T}-i_p(t)dt=\int_{t_0T-\delta}^{t_0+T}i_p(t)dt \qquad (4)$$

In the above described implementation examples, the potential of the working electrode WE is held at 0 V, i.e., common ground, using the current amplifier E3.

Non-limiting, but illustrative, values of the resistors and capacitors of the oxygen sensor 2 are presented below. The capacitance value of the capacitor C1 is not critical since the capacitor C1 is only used to temporarily retain the floating voltage before the first measurement period. Preferably, the capacitance of the capacitor C1 should not be too small so that leakage and switch capacitances affect the voltage. Correspondingly, if the capacitance is too high, the voltage follower E2 will not be able to charge the capacitor C1 to the floating voltage. In general, the capacitance of capacitor C1 is preferably within an interval of from 10 nF to 10 µF, such as 100 nF.

The capacitor C2 integrates the current during at least the last parts of the first and second measurement periods. The voltage over the capacitor C2 at the end of the measurement cycle does preferable not exceed 2.5 V in order to be within common analog to digital converter (ADC) ranges. An example of the capacitance for the capacitor C2 is 100 nF.

The output voltage of the current amplifier E3 U(E3) =R3×$i_{WE}$. The current through the resistor R2 and the capacitor C2 is then equal to U(E3)/R2=(R3/R2)×$i_{WE}$, which is the current that charges the capacitor C2 from 0 V to the end voltage that is proportional to the concentration of the dissolved oxygen.

In an embodiment, the capacitance of the capacitor C2 and the resistances of the resistors R1 and R2 are preferably chosen together to meet any requirements of the ADC input range at all currents that can arise with the specified electrode sizes and oxygen concentration ranges. Furthermore, the voltage U(E3) is preferably kept below a clipping threshold of 5V.

In an embodiment, the feedback resistor R1 is programmable within an interval of from 1 to 250 kΩ. The resistance of the resistor R2 is preferably 20 kΩ and the capacitance of the capacitor C2 is preferably 100 nF.

The implementation example shown in FIG. 4 of the oxygen sensor 2 holds the potential of the working electrode at zero and uses analog techniques to temporarily retain the floating voltage or potential on the capacitor C1 and integrates the net current response on the capacitor C2.

Figure 7:
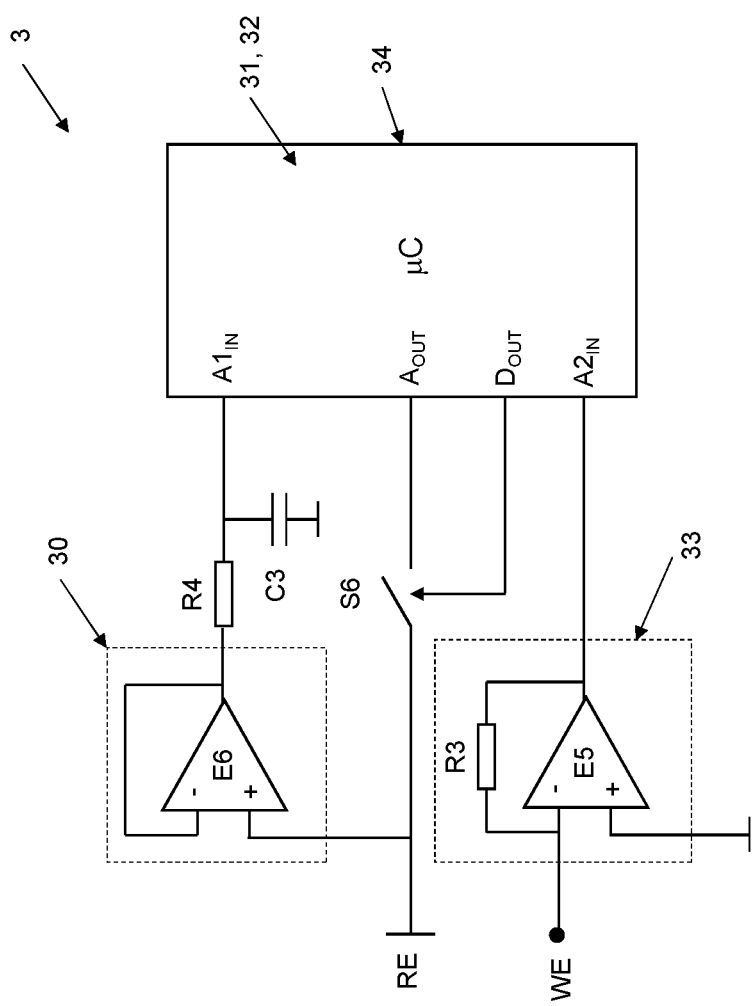
FIG. 7 is a schematic diagram of an oxygen sensor according to a further embodiment.

The circuitry of the oxygen sensor can alternatively be implemented at least partly in a digital microcontroller of signal processor as illustrated in FIG. 7.

In this implementation example, the oxygen sensor 3 comprises a processing circuitry 34, preferably a microcontroller (µC). The processing circuitry 34 comprises a first analog input $A1_{IN}$ connected to the retaining circuitry 30 and a second analog input $A2_{IN}$ connected to the generating circuitry 33. The processing circuitry 34 also comprises an analog output $A_{OUT}$ connected to the reference electrode RE. In this embodiment, the measurement voltage circuitry 31 and the floating voltage circuitry 32 are implemented in the processing circuitry 34. The processing circuitry 34 is then configured to apply, on the analog output $A_{OUT}$, the measurement voltage during the first measurement period and apply the voltage equal to the temporarily retained floating voltage during the second measurement period.

In an embodiment, the retaining circuitry 30 of FIG. 7 comprises a voltage follower E6 comprising a non-inverting input connected to the reference electrode RE, an output connected to the first analog input $A1_{IN}$ and an inverting input connected to the output of the voltage follower E6.

In an embodiment, the oxygen sensor 3 also comprises a low pass filter, such as a low pass anti-aliasing filter, connected between the retaining circuitry 30 and the first analog input $A1_{IN}$. In an embodiment, the low pass filter is implemented as a resistor R4 connected between the retaining circuitry 30 and the first analog input $A1_{IN}$ and a capacitor C3 connected between common ground and point between the resistor R4 and the first analog input $A1_{IN}$.

This optional low pass filter is arranged to reduce noise on the first analog input $A1_{IN}$. In an embodiment, the low pass filter has a cut off frequency within an interval of from 5 to 20 Hz. As an example, the capacitor C3 could have a capacitance of 100 nF and the resistor R4 has a resistance of 180 kΩ, which gives a limit at 9 Hz that significantly reduces the sensitivity for 50 Hz noise. If present in a 50 Hz noisy environment, the oxygen sensor 3 may otherwise show aliasing behavior without any low pass filter.

In an embodiment, the oxygen sensor 3 comprises a switch S6 connected between the reference electrode RE and the analog output $A_{OUT}$. In such a case, the processing circuitry 34 preferably comprises a digital output $D_{OUT}$ connected to the switch S6 and configured to output a control signal configured to close the switch S6 during the first measurement period and the second measurement period and otherwise leave the switch S6 opened.

This optional switch S6 is preferably included if the analog output $A_{OUT}$ does not have a high impedance output mode. This means that the switch S6 can thereby be used to disconnect the reference electrode RE between measurement cycles.

In the embodiment illustrated in FIG. 7, the generating circuitry 33 comprises a current amplifier E5 comprising a non-inverting input connected to common ground, an inverting input connected to the working electrode WE and an output connected to the second analog input $A2_{IN}$. The generating circuitry 33 also comprises a resistor R3, a so-called feedback resistor R3, connected between the inverting input of the current amplifier E5 and the output of the current amplifier E5.

The current amplifier E5 and the feedback resistor R3 in FIG. 7 correspond to the current amplifier E3 and the feedback resistor R1 in FIG. 4.

The processing circuitry 34 is, in an embodiment, configured to sample a voltage on the second analog input $A2_{IN}$ during at least the last part of the first measurement period and at least the last part of the second measurement period and add the sampled voltages to get a value representative of the net charge to the working electrode WE.

Figure 8:
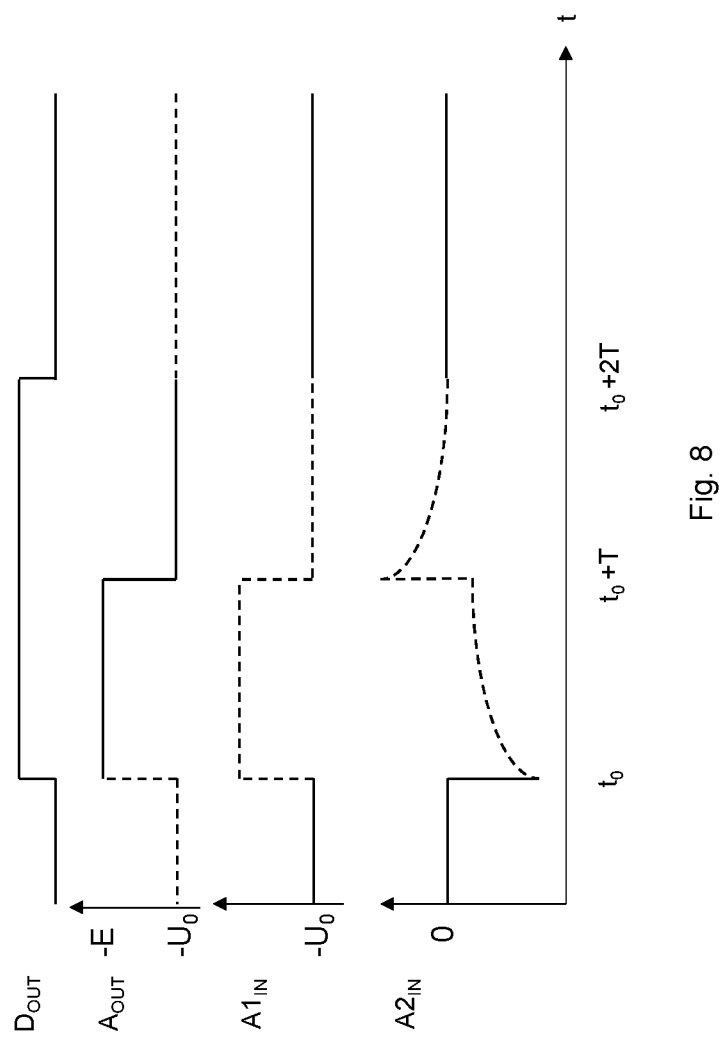
FIG. 8 schematically illustrates signals on the inputs and outputs of the microcontroller shown in FIG. 7 prior to, during and after a measurement cycle according to an embodiment.

The processing circuitry 34, such as microcontroller circuit µC, with analog inputs $A1_{IN}$ and $A2_{IN}$, analog output $A_{OUT}$ and optional digital output $D_{OUT}$ controls the potential of the reference electrode RE vs. working electrode WE and records the evoked current response i(t)=u(t)/R3 on the second analog input $A2_{IN}$, see FIG. 8. The electrical current going into the working electrode WE is transferred to a voltage u(t)=i(t)/R3 and sampled on the second analog input $A2_{IN}$. This input sampling frequency should be higher than the duration of the first and second measurement periods T. For instance, if T=10 ms the sampling frequency should be about 10 kHz. Adding the samples from $t_0$ to $t_0+2T$ will then result in a value $U(pO_2)$ proportional to the net charge Q:

$$U(pO_2)=\Sigma_{i=t_0}^{t_0+2T}u_i(t) \quad (5)$$

If only the last parts of the first and second measurement periods are used, in order to eliminate transient error effects at the potential changes, the value $U(pO_2)$ can be calculated using the following equation.

$$U(pO_2)=\Sigma_{t_0+T-\delta}^{t_0+T}u_i(t)+\Sigma_{i=t_0 2T-\delta}^{t_0+2T}u_i(t) \quad (6)$$

The feedback resistor R3 in FIG. 7 can have a resistance value as previously described herein in connection with the feedback resistor R1 in FIG. 4. Alternatively, a resistor of fixed resistance of, for instance, 2 kΩ can be used if 14 bit or more ADC is used.

In order to reduce noise further, different filters can be arranged in the data stream. Such filters can be an averaging filter, such as a finite impulse response (FIR) filter or a Butterworth filter.

FIG. 8 schematically illustrates signals on the inputs and outputs of the microcontroller shown in FIG. 7 prior to, during and after a measurement cycle according to an embodiment. The voltage on the second analog input A21N is proportional to the charge transport or electrical current to the working electrode WE. The summary of the samples between to and $t_0+2T$ will then be linearly dependent on the oxygen tension ($pO_2$), i.e., the concentration of dissolved oxygen in the liquid medium. Alternatively, the summary of the samples from $t_0+T-\delta$ to $t_0+T$ and $t_0+2T-\delta$ to $t_0+2T$ will linearly dependent on the concentration of dissolved oxygen in the liquid medium.

In an embodiment, the oxygen sensor 4, 5, see FIGS. 10 and 12, also comprises a concentration determining circuitry 45, 55. This concentration determining circuitry 45, 55 is configured to determine a value of the concentration of dissolved oxygen in the liquid medium based on the signal generated based on the measured net charge to the working electrode and a conversion function defining a conversion of a net charge value into a concentration value.

The value of the concentration of dissolved oxygen is, in an embodiment, expressed as oxygen tension or partial pressure of oxygen ($pO_2$). In such a case, the conversion function f(.) outputs the oxygen tension given an input net charge value Q, i.e., $pO_2=f(Q)$. In a particular embodiment, this oxygen tension is obtained using the following conversion function $pO_2=kQ+m$. In other words, the oxygen tension linearly depends on the net charge value.

In a particular embodiment, the conversion function, such as the values of the parameters k and m, is determined in a calibration procedure. Such a procedure involves measuring the concentration of dissolved oxygen in a liquid medium using an oxygen sensor of the embodiments and using, for instance, a blood gas analyzer at different oxygen concentrations (oxygen tensions). In such a case, the calibration function can be determined given the measured oxygen tension values from the blood gas analyzer and the measured net charge values from the oxygen sensor.

As mentioned in the foregoing, there may be a significant voltage drop in the liquid medium. In an embodiment, the conductivity of the liquid medium is therefore measured and used to compensate for this voltage drop that otherwise may affect the measurement voltage. The variation in conductance is, however, generally small as long as the geometry of the electrodes is fixed and the liquid medium surrounding the electrodes remains fairly constant, i.e., the electrodes are not moved within the liquid medium.

One way to realize this compensation is to use a function having conductance and measured reduction current as input. The voltage drop will approximately be U(liquid medium)=i($pO_2$)/G, wherein i($pO_2$) is the average current during the first measurement period. The actual reduction potential vs. Ag/AgCl is then E-U(liquid medium). There is a nearly linear relationship between the charge transfer and the reduction potential. Accordingly, it is possible to approximate the measured net charge for conductance variations.

Thus, in an embodiment the oxygen sensor 4, 5, see FIGS. 10 and 12, comprises a conductance measuring circuitry 46, 56 connected to the working electrode WE and the reference electrode RE. This conductance measuring circuitry 46, 56 is configured to measure a conductance of the liquid medium in between the working electrode WE and the reference electrode RE and generate a conductance value (G) based on the measured conductance. In this embodiment, the concentration determining circuitry 45, 55 is configured to determine the value of the concentration of dissolved oxygen in the liquid medium based on the signal generated based on the measured net charge to the working electrode, the conversion function and the conductance value. Hence, in an embodiment $pO_2=f(Q, G)$. In a particular embodiment, $pO_2=f(Q/G)$, such as $pO_2=k\times Q/G+m$.

Experimental results have shown that the net charge from the oxygen sensor is, in some applications, dependent on the conductance between the electrodes. Within the normal levels of $Na^+$ and $Cl^-$ ions in a body fluid, this dependency is small and the relation is almost linear. Accordingly, it is possible to minimize the influence of varying conductivity of the liquid medium by dividing the net charge with a factor proportional to the conductance. The electrode-liquid medium interface conductance varies with time according to protein and metal adsorption, which also has a direct influence on the measured net charge. Also spatial variations around the electrodes influence the conductance and the net charge similarly. Thus, measuring the conductance, i.e., the conductance between the working electrode WE and the reference electrode RE, is preferred to eliminate sensor dependency to conductance variations.

Measurement of conductance between two electrodes in a liquid medium is, in an embodiment, performed by a synchronous conductance measuring circuitry 46, 56. In an illustrative example, the excitation voltage during conductance measurements is a square wave signal, such as a square wave 4 kHz signal, with an amplitude of, for instance, 5 mV. Also other frequencies and amplitudes can be used for AC conductance detection. In an embodiment, the square wave signal is AC coupled with a capacitor C, see FIG. 10, to avoid net currents passing. The electrical current that goes into the working electrode WE is converted to a voltage and demodulated with a detecting circuit synchronous and in phase with the excitation voltage. The conductance is the inverse of the impedance, which similarly can be used to compensate the measured net charge for varying conductance or impedance between the working electrode WE and the reference electrode RE.

Figure 11:
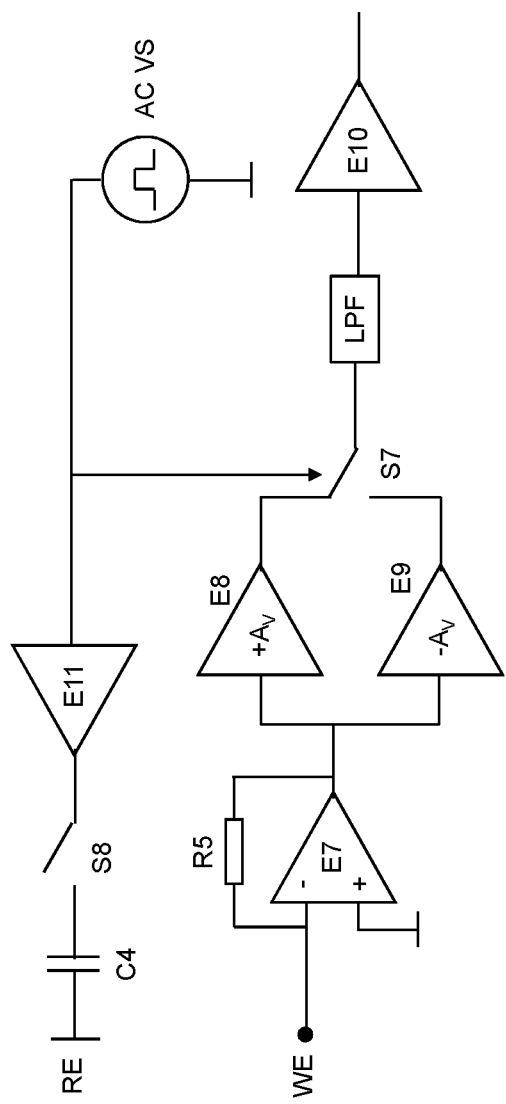
FIG. 11 is a schematic block diagram of a synchronous conductance measuring circuitry according to an embodiment.

FIG. 11 is a schematic block diagram of a synchronous conductance measuring circuitry according to an embodiment, see also FIG. 10. The conductance measurement circuitry 46 comprises an AC voltage source AC VS connected to the reference electrode RE optionally via a coupling capacitor C4, C. The conductance measurement circuitry 46 also comprises a current amplifier E7, E having a non-inverting input connected to common ground, an inverting input connected to the working electrode WE and an output. A resistor R5, R of the conductance measurement circuitry 46 is connected in parallel between the inverting input of the current amplifier E7, E and the output of the current amplifier E7, E.

In an embodiment, the conductance measurement circuitry further comprises a switch S7, a first amplifier E8 connected between the output of the current amplifier E7 and the switch S7 and a second amplifier E9 connected between the output of the current amplifier E7 and the switch S7. The first amplifier E8 and the second amplifier E9 have equal gain. The first amplifier E8 is non-inverting and the second amplifier E9 is inverting. The switch S7 is configured to switch between an output of the first amplifier E8 and an output of the second amplifier E9 in synchrony with an AC voltage of the AC voltage source AC VS.

Thus, a small defined AC voltage is delivered to the reference electrode RE via a coupling capacitor C4. The current response is detected on the current amplifier E7 and amplified further by the first and second amplifiers E8, E9 that have the same gain but the first amplifier E8 is non-inverting while the second amplifier E9 is inverting the signal. The switch S7 is switching the signal synchronously with the excitation voltage. In an embodiment, the signal is also low pass filtered in a low pass filter (LPF) and optionally amplified further in an amplifier E10.

The conductance measurement circuitry optionally comprises a second switch S8 connected between the coupling capacitor C4 and the AC voltage source AC VS to disconnect the reference electrode RE from the AC voltage source AC VS between conductance measurement cycles. An optional amplifier E11, such as 1:1000, may be arranged between the coupling capacitor C4 or the second switch S8 and the AC voltage source AC VS.

FIG. 9 schematically illustrates measurement of oxygen concentration ($pO_2$) and conductance, which are separated in time so that the excitation voltages for the $pO_2$ measurements and the conductance measurement do not interfere with each other. Thus, when the concentration of dissolved oxygen in the liquid medium is measured the square wave excitation voltage signal is turned off and when the conductance of the liquid medium is measured, no measurement voltages or voltages equal to the floating voltages are applied between the working and reference electrodes.

In an embodiment, the same current amplifier, i.e., current-to-voltage converter, can be used for the oxygen concentration and conductance measurements, which is schematically illustrated in FIG. 10. However, this is not necessary.

Another way to compensate for varying voltage drop in the liquid medium is to continuously change the measurement voltage with respect to U(liquid medium). For instance, assume that an initial measurement voltage is determined to be 0.8 V vs. Ag/AgCl. In such a case, the measurement voltage E applied during the first measurement periods is varied as E=−(0.8 V+U(liquid medium)).

Temperature changes in the liquid medium may affect the concentration of oxygen as measured using the oxygen sensor. Such temperature dependencies have serval causes. The potential of the reference electrode is dependent on the temperature according to Nernst equation. Also the conductivity is temperature dependent. Generally, the conductivity of a liquid medium increases with temperature as the mobility of ions in the liquid medium increases. The relation is, however, quite complex for complex liquid media, such as blood. Also the diffusion of oxygen molecules towards the working electrode is more rapid at increased temperatures.

In order to evaluate the temperature dependency, oxygen concentration measurements using an oxygen sensor of the embodiments can be performed in a selected liquid medium, such as blood, at different temperatures. In such a case, the relationship between the measured net charges and the temperature can be determined. This determined relation can then be used to compensate the measured net charge value for temperature variations if the temperature of the liquid medium is known.

Accordingly, in an embodiment the oxygen sensor 5, see FIG. 12, comprises a temperature measuring circuitry 57 configured to measure a temperature of the liquid medium. The temperature measuring circuitry 57 is also configured to generate a temperature value based on the measured temperature. In this embodiment, the concentration determining circuitry 55 is configured to determine the value of the concentration of dissolved oxygen in the liquid medium based on the signal generated based on the measured net charge to the working electrode, the conversion function and the temperature value. Hence, in an embodiment $pO_2$=f(Q, temperature).

In other embodiments, the concentration determining circuitry 55 is configured to determine the value of the concentration of dissolved oxygen in the liquid medium based on the signal generated based on the measured net charge to the working electrode, the conversion function, the conductance value and the temperature value, e.g., $pO_2$=f(Q, G, temperature).

FIG. 12 is a schematic block diagram of an oxygen sensor 5 according to a further embodiment. In this embodiment, the concentration determining circuitry 55 receives inputs from various circuitries of the oxygen sensor 5 and optionally external devices. For instance, the generating circuitry 55 outputs the signal generated based on the measured net charge to the working electrode, the conductance measuring circuitry 56 outputs the conductance value and the temperature measuring circuitry 57 outputs the temperature value. The concentration determining circuitry 55 optionally also receives blood gas reference data from a blood gas analyzer 60 in order to determine the conversion function. Alternatively, such reference data may have previously been determined and stored in a memory or storage 58 accessible to the concentration determining circuitry 55. This memory 58 may, for instance, contain the previously mentioned conversion function or the parameters of the conversion function to be used when determining the concentration of dissolved oxygen based in the received input values.

A monitor or screen 59 of or connected to the concentration determining circuitry 55 is configured to display the determined concentration value, such as in the form of an oxygen tension or partial pressure $pO_2$ value.

Thus, in an embodiment, a coulometric oxygen sensor 53 could be used in connection with a conductance sensor 56 and a temperature sensor 57. The timing of the oxygen and conductance measurements is controlled with a microcontroller, which also converts analog signals from the sensors to digital data that may be transferred to a computer or tablet, in which at least the concentration determining circuitry 55 may be implemented in an embodiment. In this computer, a software algorithm post-processes the data in order to compensate the net charge for varying conductance and/or temperature. Also $pO_2$ reference data from a blood gas analyzer 60 is used as target reference value to the algorithm for calculation of $pO_2$ from the raw signal.

After insertion into a blood vessel, the oxygen sensor is optionally regularly calibrated according to a known relation between oxygen tension and measured net charge.

Because the oxygen sensor is sensitive to conductance variations in the liquid medium, such as blood, a synchronous conductance sensor can be included between the working and reference electrodes. In an embodiment, a 4 kHz square wave voltage with the amplitude of a few millivolts is used for excitation between the oxygen measurements. The excitation voltage is AC coupled via a capacitor and the current to the working electrode is preferably measured using the same amplifier as for the oxygen measurements.

An aspect of the embodiments also relates to a catheter 100 comprising an oxygen sensor 1 according to any of the embodiments, see FIG. 13. In the embodiment shown in FIG. 13, the complete oxygen sensor 1 is arranged in the catheter 100.

Figure 15:
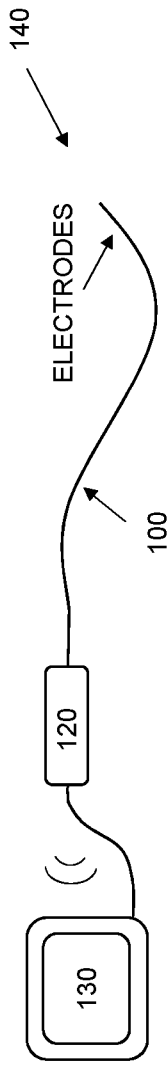
FIG. 15 is a schematic block diagram of a distal portion of a catheter according to an embodiment.
Figure 16:
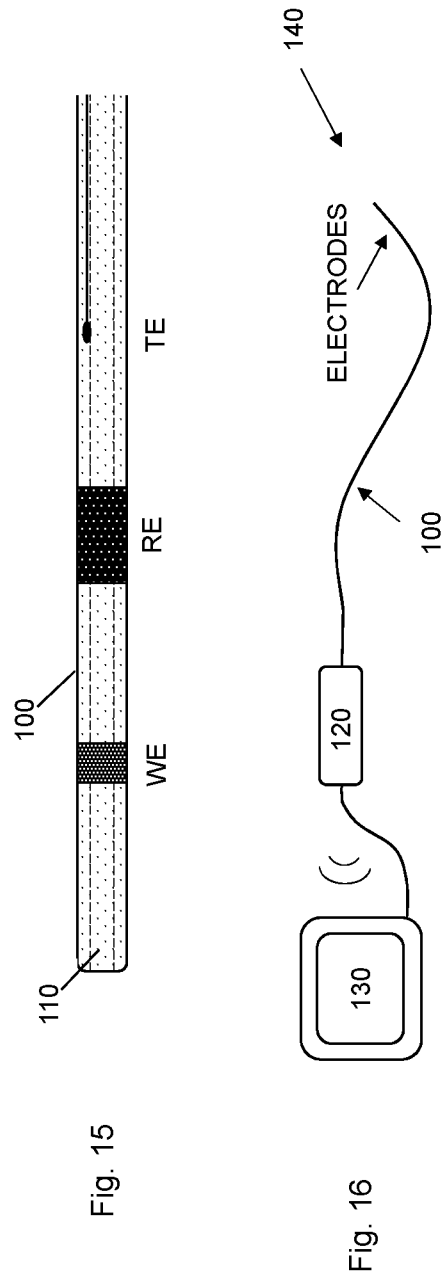
FIG. 16 is a schematic block diagram of a monitoring system according to an embodiment.

FIGS. 15 and 16 illustrate another embodiment. In this case, a monitoring system 140 is disclosed and comprises a catheter 100 comprising the working electrode WE and the reference electrode RE of an oxygen sensor according to any of the embodiments. The monitoring system 140 also comprises a processing device 120 connected to the catheter 100 and comprising the retaining circuitry, the measurement voltage circuitry, the floating voltage circuitry and the generating circuitry of the oxygen sensor. Hence, in this embodiments, electrodes of the oxygen sensor are arranged in the catheter 100, whereas the circuitries of the oxygen sensor are instead in implemented in the processing device 120.

In an embodiment, the catheter 100 may also comprise a temperature sensor, such as thermistor or thermocouple TE, used by a temperature measuring circuitry of the oxygen sensor to measure the temperature of the liquid medium.

If the oxygen sensor comprises the previously mentioned conductance measuring circuitry and/or the temperature measuring circuitry these are preferably also implemented in the processing device 120.

The oxygen concentration data is preferably transferred to a monitor 130 via a cable or wireless from the processing device 120, but a user interface can also be used to manually input the reference $pO_2$ data after taking blood samples. Pulse oximeter data ($SpO_2$) may also be displayed on the monitor 130 as safety feature for comparison of measured $SpO_2$ and calculated $pO_2$ values. If unlikely big discrepancies would occur a warning can be displayed on the monitor 130.

The analyzed liquid medium where the oxygen is measured should be a salty solution that contains chloride ions ($Cl^-$), e.g., blood, cerebrospinal fluid or saline solutions. In an embodiment, a catheter 100 with electrodes and sensors is placed with the distal end in the liquid medium, such as body fluid. The proximal end of the catheter 100 is connected to the processing device 120, which controls the circuitries of the oxygen sensor and processes measured data. Digital data is then transferred, with wire or wireless, from the processing device 120 to a monitor 130 for display.

The electrodes of the oxygen sensor may be mounted on a catheter 100 or inside a tube where the electrodes are in contact with the analyzed liquid medium. The catheter 100 may then be implanted in a living body, preferably in a blood vessel, or in a tube for ex vivo blood monitoring.

Figure 14:
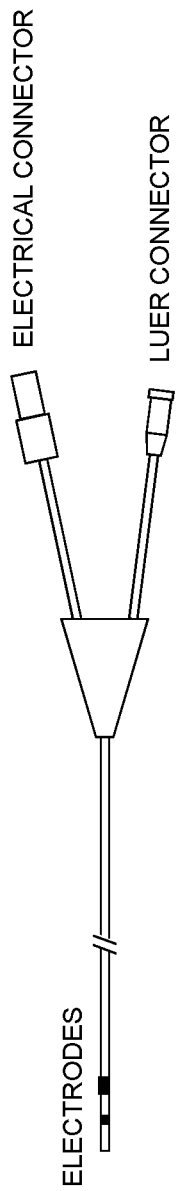
FIG. 14 is a schematic block diagram of an umbilical catheter according to an embodiment.

With reference to FIG. 14, an umbilical catheter with electrodes may be used. The catheter has two ring electrodes for oxygen measurements and optional conductance measurements, see FIG. 15. In the proximal end, an electrical connector is used to connect to the processing device 120. Also a Luer connector may be used to draw blood samples.

In an embodiment using typical umbilical catheter designs, the working electrode WE can have a surface area of 0.1-5 $mm^2$, preferably 2.5 $mm^2$ and the reference electrode RE has a surface area of 2-15 $mm^2$, preferable 10 $mm^2$, with the proviso that the surface area of the reference electrode RE is larger than the surface area of the working electrode WE. In an embodiment, the surface area of the reference electrode is 1.5-10 times larger than the surface area of the working electrode WE. The distance between the electrodes is in the embodiment 4-100 mm. The catheter 100 contains a through lumen 110 and a Luer connector in the proximal end to enable taking blood samples for analysis, infuse nutrition and medications, and to measure blood pressure. The catheter body can also contain a thermistor or temperature sensor TE for temperature monitoring as well as input to the algorithm for compensation for temperature dependency of the oxygen sensor.

It is, thus, possible to draw blood samples via the Luer connector on the catheter when the oxygen sensor is placed in the blood vessel. These blood samples may be analyzed in a blood gas analyzer and the measured $pO_2$ value, hematocrit and other blood status can be used as input to recalibrate the oxygen sensor. Because the blood cell density has an influence on the diffusion of oxygen molecules to the working electrode surface and the red blood cells will additionally buffer the oxygen level in the diffusion layer these aspects could be considered in a calibration against blood samples. A conversion function that from a given measured net charge value calculates the oxygen tension in, for instance, kPa may contain inputs from a plurality of blood gas parameters including $pO_2$, Hb or hematocrit, temperature, $Cl^-$, etc.

The cycling of the working electrode potential according to the embodiments has an advantage to the oxygen sensor. Novel electrodes are known to lose their activity towards oxygen reduction when operated continuously over extended periods of time. In addition, interference can arise from heavy metal traces, which poison the cathode, i.e., the working electrode, by electroplating at the potential where oxygen is reduced. A reconditioning procedure is therefore desirable to maintain a stable response. The working electrode is reconditioned electrochemically by applying the double voltage waveform. The waveform consists of a step during which the current for the reduction of dissolved oxygen is recorded and of another step that reconditions the WE electrode surface. Also when the conductance measurement is performed using a 4 kHz square wave a small reconditioning effect occurs.

During the first phase when oxygen is reduced on the working electrode, oxidation of the anode, i.e., the reference electrode, is forming silver chloride on the silver layer. This continuous oxidation in the $Cl^-$ ion environment maintains a very thin but important AgCl film, which stabilizes the electrical potential of the reference electrode. The potential of the reference electrode will thereby be defined by the equilibrium potential between silver and silver chloride.

Figure 19:
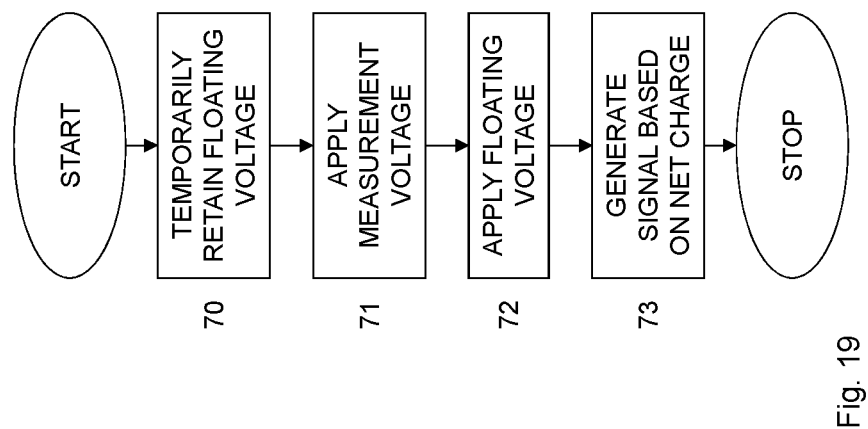
FIG. 19 is a flow chart illustrating a method for electrochemical determination of a concentration of dissolved oxygen in a liquid medium.

FIG. 19 is a flow chart illustrating a method for electrochemical determination of a concentration of dissolved oxygen in a liquid medium. The method comprises temporarily retaining, in step 70, a floating voltage between a working electrode configured to be in contact with the liquid medium and a reference electrode configured to be in contact with the liquid medium and having i) a surface area that is equal to or larger than a surface area of the working electrode, and ii) a surface made of Ag/AgCl. The method also comprises applying, in step 71, a measurement voltage between the working electrode and the reference electrode during a first measurement period causing dissolved oxygen in the liquid medium to react by reduction at a surface of the working electrode to produce an evoked current into the working electrode. The method further comprises applying, in step 72, a voltage between the working electrode and the reference electrode equal to the temporarily retained floating voltage during a second measurement period immediately following and of an equal duration as the first measurement period to produce a current out from the working electrode. The method further comprises generating, in step 73, a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

Figure 20:
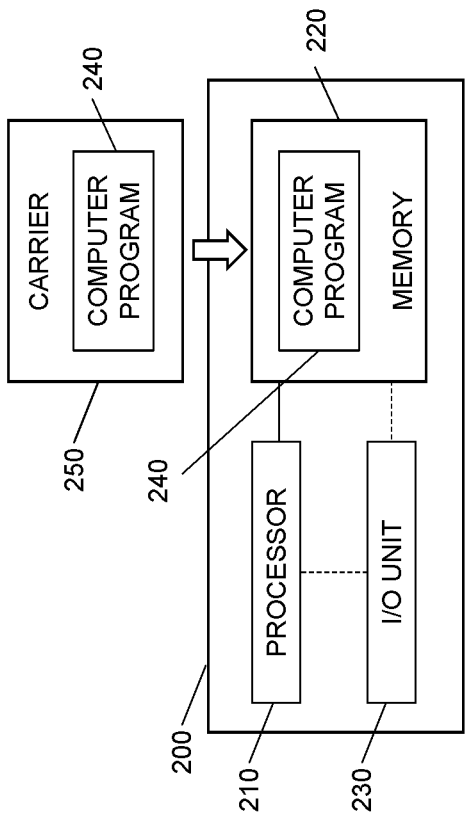
FIG. 20 is a schematic block diagram of a computer program based implementation according to an embodiment.

FIG. 20 is a schematic block diagram of a computer program based implementation 200 according to an embodiment. In this particular example, at least some of the steps, functions, procedures, circuitries and/or blocks described herein are implemented in a computer program 240, which is loaded into the memory 220 for execution by processing circuitry including one or more processors 210. The processor(s) 210 and memory 220 are interconnected to each other to enable normal software execution. An optional I/O unit 230 may also be interconnected to the processor(s) 210 and/or the memory 220 to enable input and/or output of relevant data.

The term 'processor' should be interpreted in a general sense as any circuitry, system or device capable of executing program code or computer program instructions to perform a particular processing, determining or computing task.

The processing circuitry including one or more processors 210 is thus configured to perform, when executing the computer program 240, well-defined processing tasks such as those described herein.

The processing circuitry does not have to be dedicated to only execute the above-described steps, functions, procedure and/or blocks, but may also execute other tasks.

In a particular embodiment, the computer program 240 comprises instructions, which when executed by at least one processor 210, cause the at least one processor 210 to temporarily retain a floating voltage between a working electrode configured to be in contact with a liquid medium comprising dissolved oxygen and a reference electrode configured to be in contact with the liquid medium and having i) a surface area that is equal to or larger than a surface area of the working electrode, and ii) a surface made of Ag/AgCl. The at least one processor 210 is also caused to control a voltage source to apply a measurement voltage between the working electrode and the reference electrode during a first measurement period causing dissolved oxygen in the liquid medium to react by reduction at a surface of the working electrode to produce an evoked current into the working electrode. The at least one processor 210 is further caused to control the voltage source to apply a voltage between the working electrode and the reference electrode equal to the temporarily retained floating voltage during a second measurement period immediately following and of an equal duration as the first measurement period to produce a current out from the working electrode. The at least one processor 210 is additionally caused to generate a signal representative of the concentration of dissolved oxygen in the liquid medium based on a measured net charge to the working electrode equal to a sum of a charge transferred to the working electrode during at least a last part of the first measurement period and a charge transferred to the working electrode during at least a last part of the second measurement period.

The proposed technology also provides a carrier 250 comprising the computer program 240. The carrier 250 is one of an electronic signal, an optical signal, an electromagnetic signal, a magnetic signal, an electric signal, a radio signal, a microwave signal, or a computer-readable storage medium.

By way of example, the software or computer program 240 may be realized as a computer program product, which is normally carried or stored on a computer-readable medium 250, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program 240 may thus be loaded into the operating memory 220 of a device 200 for execution by the processing circuitry 210 thereof.

Figure 17:
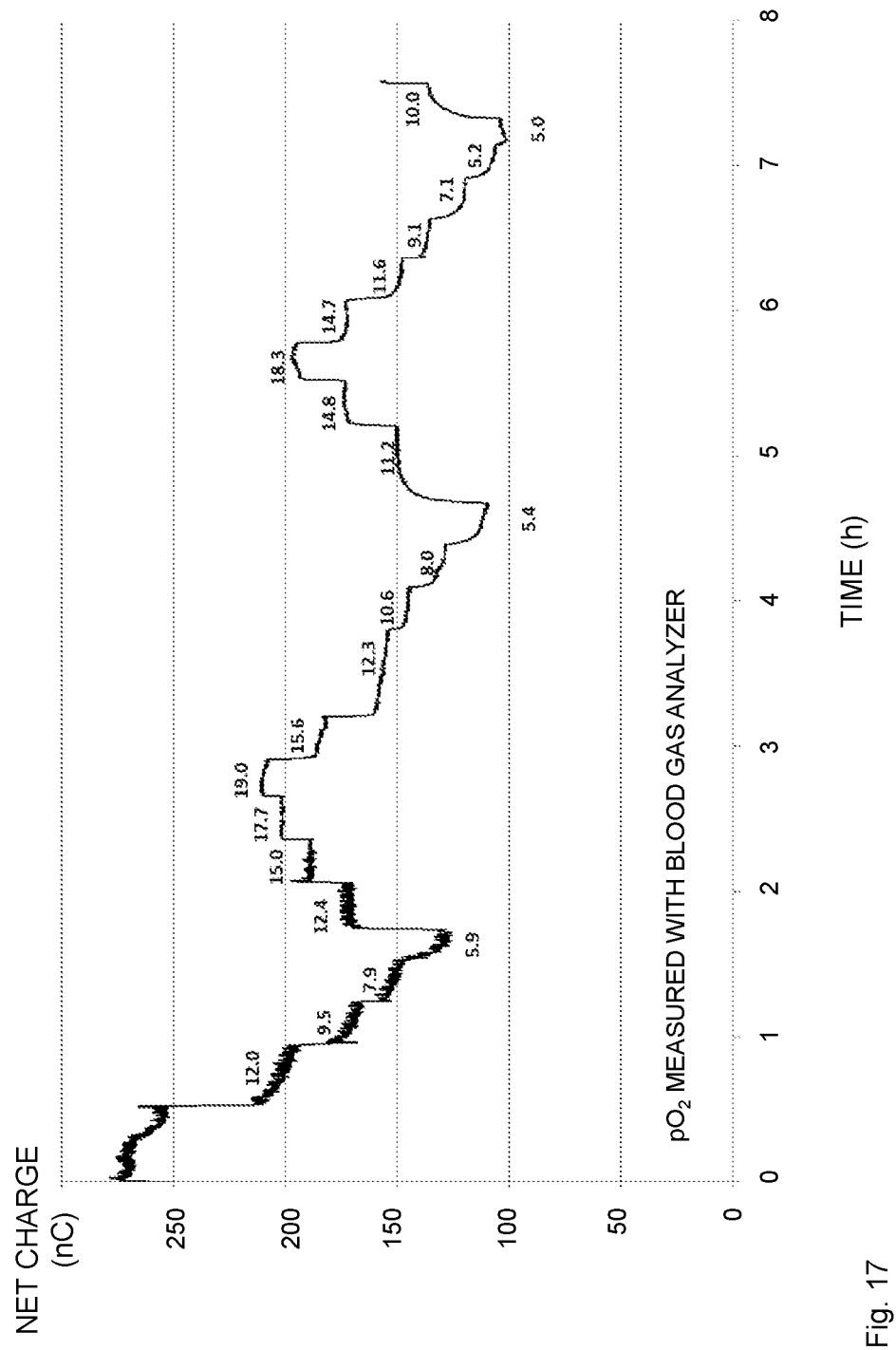
FIG. 17 is a diagram illustrating in vivo recording of a raw sensor signal using a catheter according to an embodiment from a porcine aorta during 8 hours.

An oxygen sensor of the embodiment with gold working electrode and Ag/AgCl reference electrode was tested in vivo using a porcine model. The porcine subject was anesthetized and kept in narcosis intravenously during eight hours, while it was artificially ventilated with different gas mixtures of nitrogen and oxygen. The net charge Q from an oxygen sensor of the embodiments and blood gas reference data is displayed in FIG. 17. A four hour settling time was observed for the oxygen sensor. FIG. 17 indicates the net charge as measured by the oxygen sensor together with $pO_2$ values as measured by a blood gas analyzer.

Figure 18:
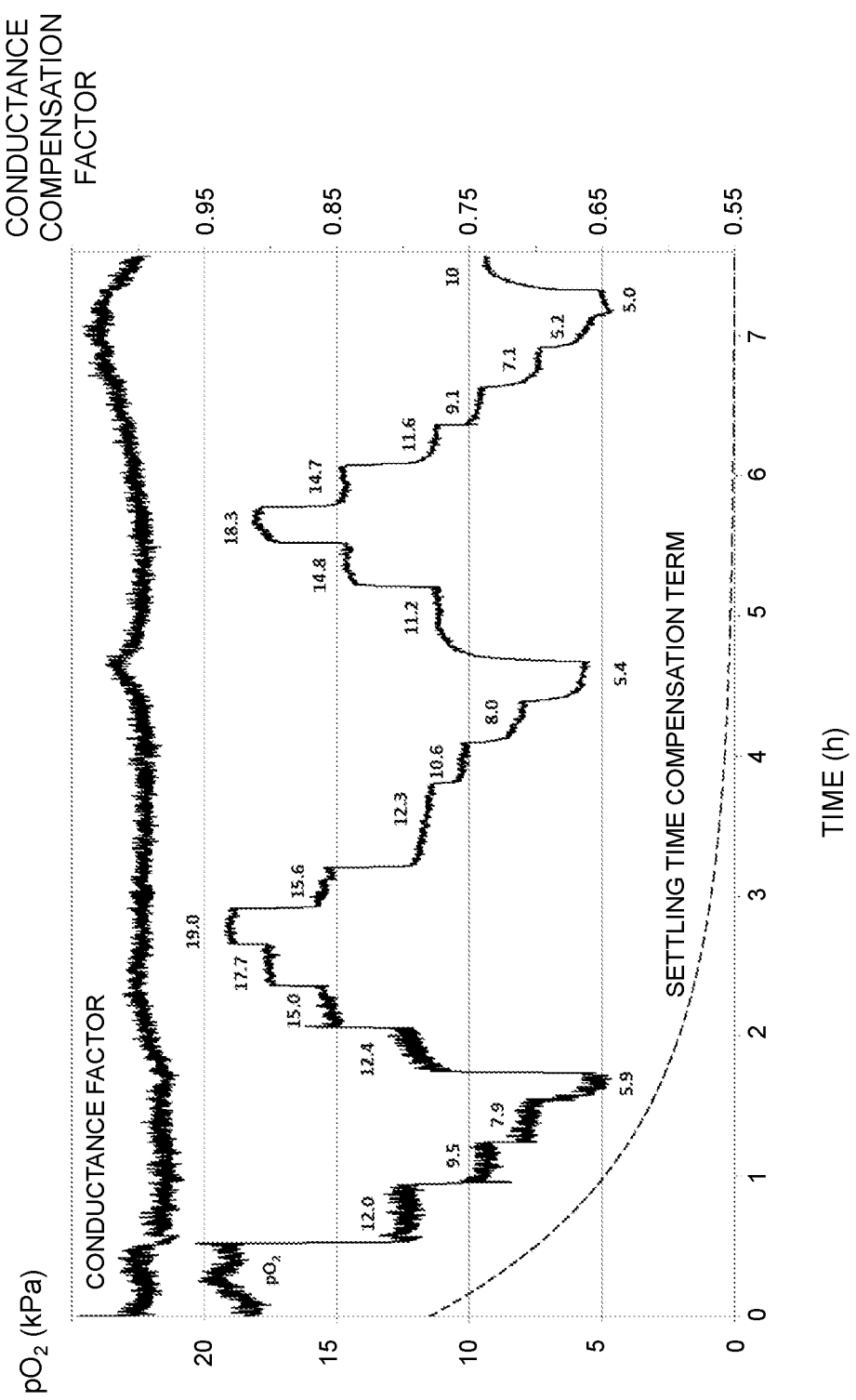
FIG. 18 is a diagram illustrating compensated $pO_2$ data according to an embodiment.

The raw net charge signal was thereafter post-processed by subtracting a settling time component from the raw net charge signal. The resulting signal was divided with the normalized conductance value. The final $pO_2$ result is shown in FIG. 18, which verifies the feasibility of the oxygen sensor.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An oxygen sensor configured for electrochemical determination of a concentration of dissolved oxygen in a liquid medium, said oxygen sensor comprising:
   a working electrode configured to be in contact with said liquid medium;
   a reference electrode configured to be in contact with said liquid medium and having i) a surface area that is equal to or larger than a surface area of said working electrode, and ii) a surface made of Ag/AgCl;
   a retaining circuitry configured to temporarily retain a floating voltage between said working electrode and said reference electrode;
   a measurement voltage circuitry comprising a voltage source configured to apply a measurement voltage between said working electrode and said reference electrode during a first measurement period causing dissolved oxygen in said liquid medium to react by reduction at a surface of said working electrode to produce an evoked current into said working electrode;

a floating voltage circuitry configured to apply a voltage between said working electrode and said reference electrode equal to said temporarily retained floating voltage during a second measurement period immediately following and of an equal duration as said first measurement period to produce a current out from said working electrode; and a generating circuitry configured to generate a signal representative of said concentration of dissolved oxygen in said liquid medium based on a measured net charge to said working electrode equal to a sum of a charge transferred to said working electrode during at least a last part of said first measurement period and a charge transferred to said working electrode during at least a last part of said second measurement period, wherein said oxygen sensor does not comprise a counter electrode.

2. The oxygen sensor according to claim 1, wherein said surface of said working electrode is made of a conductive material selected from a group consisting of gold, silver and carbon.

3. The oxygen sensor according to claim 1, wherein a relationship of said surface area of said working electrode and said surface area of said reference electrode is within an interval of from 1:2 to 1:5.

4. The oxygen sensor according to claim 1, wherein said equal duration of said first measurement period and said second measurement period is selected within an interval of from 5 to 20 ms.

5. The oxygen sensor according to claim 4, wherein said equal duration of said first measurement period and said second measurement period is selected within an interval of from 7 to 15 ms.

6. The oxygen sensor according to claim 1, wherein said measurement voltage circuitry is configured to apply a measurement voltage within an interval of from −0.5 to −1.4 V between said working electrode and said reference electrode during said first measurement period.

7. The oxygen sensor according to claim 1, wherein said generating circuitry is configured to generate said signal representative of said concentration of dissolved oxygen in said liquid medium based on a measured net charge to said working electrode equal to a sum of a charge transferred to said working electrode during said first measurement period and a charge transferred to said working electrode during said second measurement period.

8. The oxygen sensor according to claim 1, wherein said generating circuitry is configured to generate said signal representative of said concentration of dissolved oxygen in said liquid medium based on a measured net charge to said working electrode equal to a sum of a charge transferred to said working electrode during said last part of said first measurement period and a charge transferred to said working electrode during said last part of said second measurement period.

9. The oxygen sensor according to claim 1, further comprising a processing circuitry comprising:
a first analog input connected to said retaining circuitry;
a second analog input connected to said generating circuitry;
an analog output connected to said reference electrode; and
said measurement voltage circuitry and said floating voltage circuitry, wherein said processing circuitry is configured to apply, on said analog output, said measurement voltage during said first measurement period and apply said voltage equal to said temporarily retained floating voltage during said second measurement period.

10. The oxygen sensor according to claim 9, wherein said retaining circuitry is a voltage follower comprising:
a non-inverting input connected to said reference electrode;
an output connected to said first analog input; and
an inverting input connected to said output of the voltage follower.

11. The oxygen sensor according to claim 9, further comprising a low pass filter connected between said retaining circuitry and said first analog input.

12. The oxygen sensor according to claim 9, further comprising a switch connected between said reference electrode and said analog output, wherein said processing circuitry comprises a digital output connected to said switch and configured to output a control signal configured to close said switch during said first measurement period and said second measurement period and otherwise leave said switch opened.

13. The oxygen sensor according to claim 9, wherein said generating circuitry comprises:
a current amplifier comprising:
a non-inverting input connected to common ground;
an inverting input connected to said working electrode; and
an output connected to said second analog input; and
a feedback resistor connected between said inverting input of said current amplifier and said output of said current amplifier.

14. The oxygen sensor according to claim 9, wherein said processing circuitry is configured to sample a voltage on said second analog input during said at least a last part of said first measurement period and said at least a last part of said second measurement period and add said sampled voltages to get a value representative of said net charge to said working electrode.

15. The oxygen sensor according to claim 1, wherein said retaining circuitry comprises:
a voltage follower having a non-inverting input connected to said reference electrode and an output connected to an inverting input of said voltage follower;
a switch; and
a capacitor connected between common ground and said switch, wherein said switch is connected between said capacitor and said inverting input of said voltage follower.

16. The oxygen sensor according to claim 15, further comprising a resistor connected between said capacitor and said output of said voltage follower, said resistor and said capacitor forming a low pass filter.

17. The oxygen sensor according to claim 1, wherein said measurement voltage circuitry and said floating voltage circuitry comprise:
a first switch;
said voltage source connected between common ground and said first switch;
an operational amplifier having a non-inverting input connected to said first switch, an inverting input connected to said reference electrode and an output connected to said reference electrode via a second switch; and
a third switch connected between i) a point between said first switch and said non-inverting input of said operational amplifier and ii) said retaining circuitry.

18. The oxygen sensor according to claim 1, wherein said generating circuitry comprises:
- a current amplifier having a non-inverting input connected to common ground, an inverting input connected to said working electrode and an output connected to a first switch;
- a first feedback resistor connected between said inverting input of said current amplifier and said output of said current amplifier;
- a sample-and-hold circuit; and
- a second resistor connected between said first switch and said sample-and-hold circuit,
- wherein said sample-and-hold circuit comprises:
  - an operational amplifier having a non-inverting input connected to common ground, an inverting input connected to said second resistor, and an output;
  - a capacitor connected between said inverting input of said operational amplifier and said output of said operational amplifier; and
  - a second switch connected between said inverting input of said operational amplifier and said output of said operational amplifier.

19. The oxygen sensor according to claim 1, further comprising a concentration determining circuitry configured to determine a value of said concentration of dissolved oxygen in said liquid medium based on said signal and a conversion function defining a conversion of a net charge value into a concentration value.

20. The oxygen sensor according to claim 19, further comprising a conductance measuring circuitry connected to said working electrode and said reference electrode and configured to measure a conductance of said liquid medium in between said working electrode and said reference electrode and generate a conductance value based on said measured conductance, wherein said concentration determining circuitry is configured to determine said value of said concentration of dissolved oxygen in said liquid medium based on said signal, said conversion function and said conductance value.

21. The oxygen sensor according to claim 20, wherein said conductance measurement circuitry comprises:
- an AC voltage source connected to said reference electrode;
- a current amplifier having a non-inverting input connected to common ground, an inverting input connected to said working electrode and an output; and
- a resistor connected in parallel between said inverting input of said current amplifier and said output of said current amplifier.

22. The oxygen sensor according to claim 21, wherein said conductance measurement circuitry further comprises:
- a switch;
- a first amplifier connected between said output of said current amplifier and said switch; and
- a second amplifier connected between said output of said current amplifier and said switch, said first amplifier and said second amplifier having equal gain,
- wherein said first amplifier is non-inverting and said second amplifier is inverting, and wherein said switch is configured to switch between an output of said first amplifier and an output of said second amplifier in synchrony with an AC voltage of said AC voltage source.

23. The oxygen sensor according to claim 19, further comprising a temperature measuring circuitry configured to measure a temperature of said liquid medium and generate a temperature value based on said measured temperature, wherein said concentration determining circuitry is configured to determine said value of said concentration of dissolved oxygen in said liquid medium based on said signal, said conversion function and said temperature value.

24. A catheter comprising an oxygen sensor according to claim 1.

25. A monitoring system comprising a catheter, a processing device and the oxygen sensor according to claim 1,
- the catheter comprising said working electrode and said reference electrode of the oxygen sensor; and
- the processing device being connected to said catheter and comprising said retaining circuitry, said measurement voltage circuitry, said floating voltage circuitry and said generating circuitry of said oxygen sensor.

\* \* \* \* \*